US012279885B2

(12) United States Patent
Billi et al.

(10) Patent No.: US 12,279,885 B2
(45) Date of Patent: Apr. 22, 2025

(54) SYSTEM FOR HEALTH MONITORING ON PROSTHETIC AND FIXATION DEVICES

(71) Applicant: THE REGENTS OF THE UNIVERSITY OF CALIFORNIA, Oakland, CA (US)

(72) Inventors: Fabrizio Billi, Los Angeles, CA (US); Per Henrik Borgstrom, Sacramento, CA (US); William Kaiser, Los Angeles, CA (US); Harry A McKellop, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 18/673,230

(22) Filed: May 23, 2024

(65) Prior Publication Data

US 2024/0306990 A1 Sep. 19, 2024

Related U.S. Application Data

(60) Continuation of application No. 18/351,409, filed on Jul. 12, 2023, now Pat. No. 11,992,335, which is a
(Continued)

(51) Int. Cl.
*A61B 5/00* (2006.01)
*A61B 5/11* (2006.01)
(Continued)

(52) U.S. Cl.
CPC .......... *A61B 5/4851* (2013.01); *A61B 5/1121* (2013.01); *A61B 5/1122* (2013.01);
(Continued)

(58) Field of Classification Search
None
See application file for complete search history.

(56) References Cited

U.S. PATENT DOCUMENTS

| 5,170,666 A | 12/1992 | Larsen |
| 5,819,007 A | 10/1998 | Elghazzawi |

(Continued)

FOREIGN PATENT DOCUMENTS

| JP | 2010-051416 | 3/2010 |
| KR | 10/2008/0057352 | 6/2008 |

OTHER PUBLICATIONS

Bowdler, "Prototype Device to Spot Knee Osteoarthritis Unveiled," BBC News, 2010, http://www.bbc.com/news/health-10630883, accessed Mar. 4, 2013, 2 pages.
(Continued)

*Primary Examiner* — Jason M Ip
(74) *Attorney, Agent, or Firm* — Foley & Lardner LLP

(57) ABSTRACT

A monitoring apparatus for a human body includes a node network with at least one motion sensor and at least one acoustic sensor. A processor is coupled to the node network, and receives motion information and acoustic information from the node network. The processor determines from the motion information and the acoustic information a source of acoustic emissions within the human body by analyzing the acoustic information in the time domain to identify an event envelope representing an acoustic event, determining a feature vector related to the event envelope, calculating a distance between the feature vector and each of a set of predetermined event silhouettes, and identifying one of the predetermined event silhouettes for which the distance is a minimum.

18 Claims, 23 Drawing Sheets

Related U.S. Application Data division of application No. 16/906,632, filed on Jun. 19, 2020, now Pat. No. 11,712,201, which is a continuation of application No. 14/773,253, filed as application No. PCT/US2014/021305 on Mar. 6, 2014, now abandoned.

(60) Provisional application No. 61/774,460, filed on Mar. 7, 2013.

(51) Int. Cl.
    *A61B 7/00* (2006.01)
    *G16H 40/63* (2018.01)
    *G16H 50/20* (2018.01)

(52) U.S. Cl.
    CPC .......... *A61B 5/4528* (2013.01); *A61B 5/6812* (2013.01); *A61B 5/7282* (2013.01); *A61B 7/006* (2013.01); *G16H 40/63* (2018.01); *G16H 50/20* (2018.01); *A61B 5/4514* (2013.01); *A61B 5/7264* (2013.01); *A61B 2560/0475* (2013.01); *A61B 2562/0204* (2013.01)

(56) References Cited

U.S. PATENT DOCUMENTS

| | | |
|---|---|---|
| 6,386,038 B1 | 5/2002 | Lewis et al. |
| 6,594,382 B1 | 7/2003 | Woodall |
| 2003/0091203 A1 | 5/2003 | Croft et al. |
| 2006/0047283 A1 | 3/2006 | Evans et al. |
| 2007/0088194 A1 | 4/2007 | Tahar et al. |
| 2007/0118054 A1 | 5/2007 | Pinhas et al. |
| 2007/0265533 A1 | 11/2007 | Tran |
| 2007/0273504 A1 | 11/2007 | Tran |
| 2007/0276270 A1 | 11/2007 | Tran |
| 2008/0001735 A1 | 1/2008 | Tran |
| 2010/0298650 A1 | 11/2010 | Moon et al. |
| 2010/0305481 A1 | 12/2010 | Igney et al. |
| 2012/0029345 A1 | 2/2012 | Mahfouz et al. |
| 2012/0203491 A1 | 8/2012 | Sun et al. |
| 2012/0245481 A1 | 9/2012 | Blanco et al. |
| 2013/0021259 A1 | 1/2013 | Sudo et al. |
| 2013/0041289 A1 | 2/2013 | Sena et al. |
| 2013/0095459 A1 | 4/2013 | Tran |
| 2013/0172691 A1 | 7/2013 | Tran |
| 2013/0211259 A1 | 8/2013 | Komistek et al. |
| 2013/0226020 A1 | 8/2013 | Holley et al. |
| 2015/0045699 A1 | 2/2015 | Mokaya et al. |
| 2015/0190091 A1 | 7/2015 | Ser et al. |
| 2016/0287122 A1 | 10/2016 | Heneghan |
| 2017/0234837 A1 | 8/2017 | Hall et al. |
| 2018/0289324 A1 | 10/2018 | Kianifar et al. |

OTHER PUBLICATIONS

International Search Report for International Application No. PCT/US2014/021305 mailed Jun. 27, 2014, 3 pages.

Popescu et al., "An Acoustic Fall Detector System that Uses Sound Height Information to Reduce the False Alarm Rate," 30th Annual International IEEE EMBS Conference, Vancouver, British Columbia, Canada, Aug. 20-24, 2008, pp. 4628-4631.

www.acousticemission.net, "Medical Applications for Acoustic Emission," Cardiff University, 2006, accessed Mar. 4, 2013, 2 pages.

www.healio.com, "New Device Could Predict Impending Stress Fractures Through Acoustic Emissions," Orthopedics Today, Nov. 2006, accessed Mar. 4, 2013, 4 pages.

|   | A | B | C | D | E |
|---|---|---|---|---|---|
| A |   |   |   |   |   |
| B | 2 |   |   |   |   |
| C | 4 | 4 |   |   |   |
| D | 6 | 6 | 6 |   |   |
| E | 6 | 6 | 6 | 4 |   |

*FIG. 14A*

|    | AB | C | D | E |
|----|----|---|---|---|
| AB |    |   |   |   |
| C  | 4  |   |   |   |
| D  | 6  | 6 |   |   |
| E  | 6  | 6 | 4 |   |

*FIG. 14B*

|    | AB | C | DE |
|----|----|---|----|
| AB |    |   |    |
| C  | 4  |   |    |
| DE | 6  | 6 |    |

*FIG. 14C*

|     | ABC | DE |
|-----|-----|----|
| ABC |     |    |
| DE  | 6   |    |

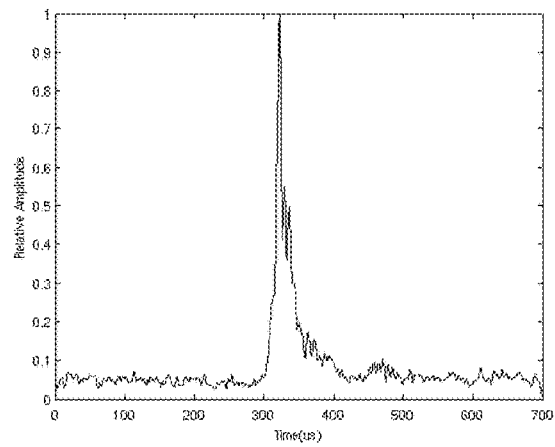
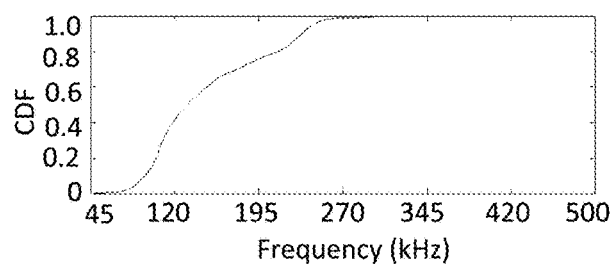
*FIG. 28A*  *FIG. 28B*
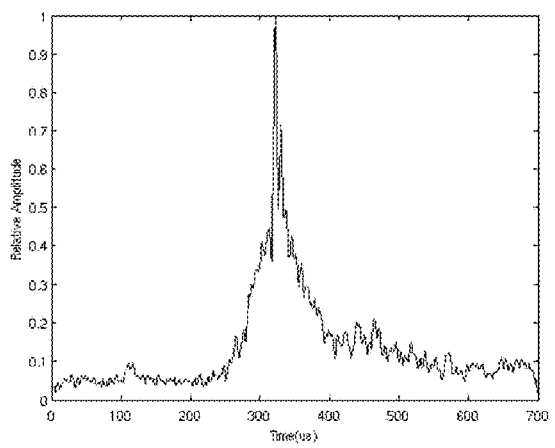
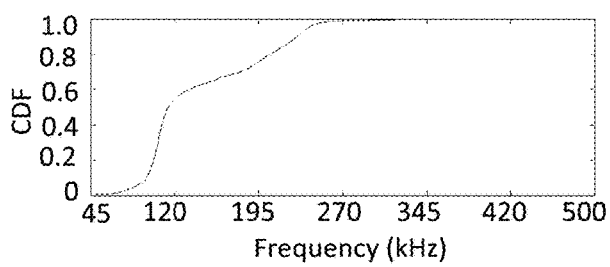
*FIG. 29A*  *FIG. 29B*

SYSTEM FOR HEALTH MONITORING ON PROSTHETIC AND FIXATION DEVICES

CROSS-REFERENCE TO RELATED PATENT APPLICATION

This application is a continuation of U.S. application Ser. No. 18/351,409 filed Jul. 12, 2023, now U.S. Pat. No. 11,992,335, which application is a divisional application of U.S. application Ser. No. 16/906,632 filed Jun. 19, 2020, which application is a continuation application of U.S. application Ser. No. 14/773,253, filed Sep. 4, 2015, which application is a National Stage Entry of PCT/US2014/021305, filed Mar. 6, 2014, which application claims the benefit of U.S. Provisional Patent Applications No. 61/774,460 filed Mar. 7, 2013 to Billi et al., titled "SYSTEM FOR HEALTH MONITORING ON PROSTHETIC AND FIXATION DEVICES," the contents of which are incorporated herein by reference in their entirety.

BACKGROUND

Current diagnostic techniques for the human body do not detect some problems until they have progressed into advanced stages, at which point irreparable damage may already have occurred. Damage may occur from a failure to detect problems affecting natural or artificial joints, the spine, bone, cartilage, or other tissue.

For example, the spine can be affected by arthritis, degenerative wear and tear on joints and disks, scoliosis, and a variety of other abnormalities that cause pain, numbness and weakness. Problems in the lower back or lumbar spine can affect the leg and foot, while problems in the cervical spine of the neck can affect the arms and hands. The causes of back pain can be very complex, and it is often difficult to get an accurate diagnosis. However, getting an accurate diagnosis of the cause of back pain is important, because different diagnoses may require very different treatment approaches Similarly, diagnosis and treatment for joints, bone, cartilage, or other tissue will vary by cause.

Additionally, total joint replacement has become a widely accepted treatment for many destructive joint diseases including osteoarthritis, rheumatoid arthritis, osteonecrosis and severe pathologic fractures. Joint replacement implants may eventually fail if subjected to prolonged or high stress. Artificial joints, especially weight-bearing implants such as hip and knee joints, are unable to withstand overly vigorous activities, and excessive stress can limit their durability. Failures may occur due to implant loosening or due to osteolysis, which is the loss or degradation of bone surrounding an implant. These two failure mechanisms are intimately related in a joint replacement implant and, for the most part, are due to wear of the weight-bearing surfaces of a joint because wear of the joint generates debris. In response to this debris, a biological reaction occurs that eventually leads to osteolysis and implant loosening. These failures frequently require surgical revision, which can be severely complicated by advanced levels of joint degradation.

Thus, it would be beneficial to have an improved capability for detection and monitoring of status of natural or artificial joints, the spine, bone, cartilage, or other tissue.

SUMMARY

A monitoring apparatus for a human body includes a node network with at least one motion sensor and at least one acoustic sensor. A processor is coupled to the node network, and receives motion information and acoustic information from the node network. The processor determines from the motion information and the acoustic information a source of acoustic emissions within the human body by analyzing the acoustic information in the time domain to identify an event envelope representing an acoustic event, determining a feature vector related to the event envelope, calculating a distance between the feature vector and each of a set of predetermined event silhouettes, and identifying one of the predetermined event silhouettes for which the distance is a minimum.

BRIEF DESCRIPTION OF THE DRAWINGS

FIGS. 14A-D illustrate an example of clustering.

FIGS. 14E-I illustrate an example of dendrogram construction for the clustering example.

FIGS. 28A-B illustrate an example of a sensor signal (FIG. 28A) and CDF (FIG. 28B).

FIGS. 29A-B illustrate an example of a noise signal (FIG. 29A) and CDF (FIG. 29B).

DETAILED DESCRIPTION

Figure 1A:
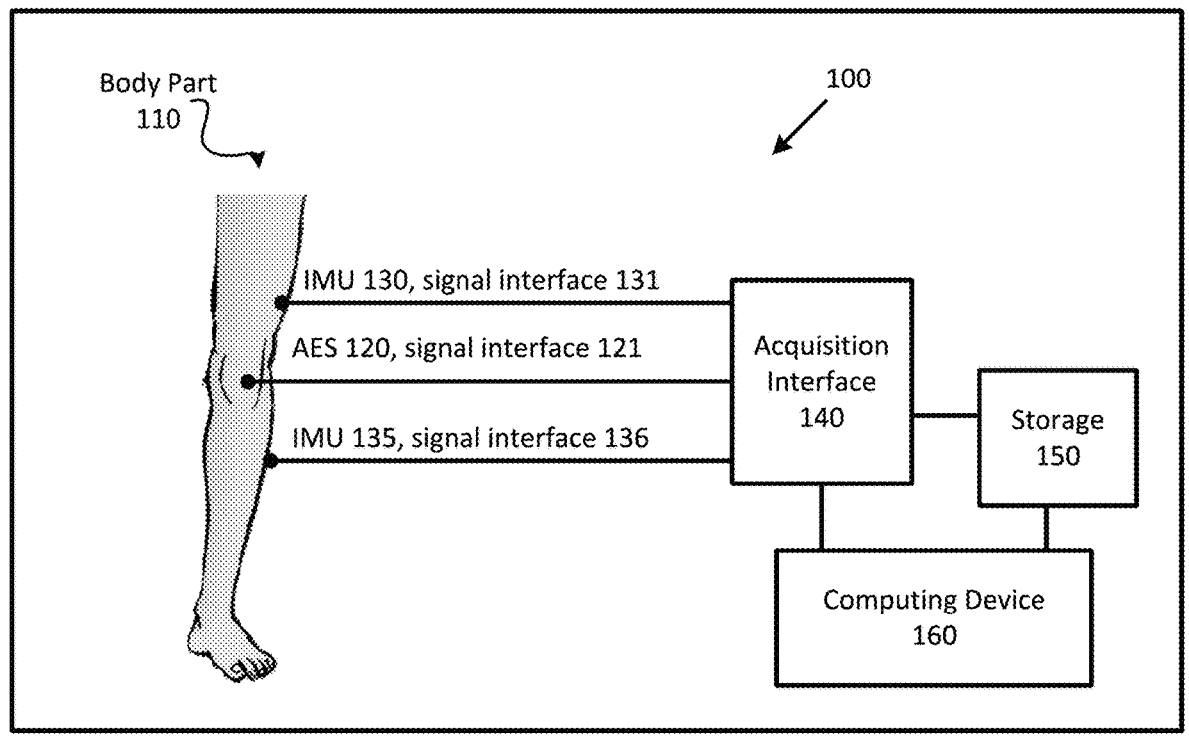
FIG. 1A illustrates an example of a monitoring system.

Early detection and diagnosis using a monitoring device allows preventative intervention through physical therapy, medication, dietary supplements, earlier revision surgery, or other measures. For example, rather than eliminating a particular activity entirely, a doctor can suggest modified activities based on actual knowledge of a condition. Monitoring of a patient's body may provide early indication of conditions that could lead to joint, bone, or tissue damage. Monitoring also provides information regarding healing processes. In this disclosure, a monitoring system is described that is useful for monitoring both natural and artificial structures and materials. The disclosed monitoring system may be positioned external to the body, or may be partially or fully implanted within the body.

Some implementations of the disclosed system may be used to monitor prosthetic devices or fixation devices. Prosthetic devices may be implanted or externally applied, and may be removable structures. Examples of externally applied prosthetic devices include braces and artificial limbs. Examples of implanted prosthetic devices include joint, bone, cartilage, or ligament replacements, cosmetic implants, and artificial organs or portions of organs, such as heart valves. Fixation devices are internally or externally applied, and may or may not be removable or removed. Some examples of fixation devices include rods, screws, plates, pins, and wires, any of which may be left in a patient for a time during healing, or may be intended for permanent placement.

In addition to monitoring prosthetic devices and fixation devices, implementations of the disclosed system may be used to monitor joints, the spine, bone, cartilage, organs, or any other structure. For example, the system may be used for monitoring gastrointestinal disorders, respiratory disorders, and cardiovascular disorders such as coronary and artery diseases. In some implementations, a system may be placed or implanted near a structure of interest, such as near a blood vessel, organ, bowel, or other structure.

A monitoring system according to this disclosure is referred to as a SEARI (Sensor Enabled Adverse Event Recognition and Identification) system. Information provided by the SEARI system may be used for detection of problem conditions, and for quantification and evaluation of treatment efficacy. For example, a monitoring device may be used to measure the effects of drugs on cartilage, and thereby expedite development of cartilage-boosting drugs. In some situations, a SEARI system may be used instead of costly imaging techniques such as magnetic resonance imaging (MRI).

In a SEARI system, technologically advanced sensors, low-power integrated circuits, and wireless communications are used in low-cost, miniature, lightweight, and intelligent physiological sensor nodes. These nodes are capable of sensing, processing, and communicating a variety of physiological parameters. Networks of nodes allow inexpensive, continuous health monitoring. Nodes may be implanted, connected to a fixation device or connected to a prosthetic device. A SEARI system integrates acoustic emission (AE) detection technology and physiological sensors, and incorporates energy and data optimization techniques to support long-term continuous monitoring and detection. A battery, which may be rechargeable, allows for untethered monitoring by a SEARI system. Data may be downloaded via a wired or wireless communication interface. A SEARI system may be fully or partially implanted.

FIG. 1A illustrates an example of a SEARI system 100, shown as being used with respect to body part 110, in this illustration a leg. Detection is illustrated for the knee joint by way of example only, and could additionally or alternatively be for a joint on another portion of the leg or a joint on another body part 110.

One or more AE sensors (collectively AES 120) are positioned on or around the area of the kneecap in the example of FIG. 1A. Electrical signals from AES 120 are provided over signal interface 121. In general, multiple AE sensors of AES 120 may be spatially distributed around an area of interest, such as on the skin around a joint and/or internally near or at the joint or other position. By sampling the multiple AE sensors and adjusting, for example, for propagation delay, an AE source may be located and identified.

AE may be in a frequency range, such as a frequency range including sonic and/or ultrasonic frequencies, or other frequency range. For example, AE may be in the range 1 kHz to 100 MHz, 1 kHz to 20 kHz, 10 kHz to 100 kHz, 100 kHz to 500 kHz, 100 kHz to 1 MHz, 100 kHz to 10 MHz, 1 MHz to 2 MHz, 1 MHz to 10 MHz, 1 MHz to 100 MHz, 10 MHz to 100 MHz, less than 1 kHz, greater than 1 MHz, greater than 10 MHz, less than 100 MHz, greater than 100 MHz, frequencies excluding a band in any of the above ranges, and other ranges. A frequency range of interest may be a narrow band around a frequency of interest, or excluding a narrow band around a certain frequency. Sensors of AES 120, with optional related filtering, are selected for the AE range of interest.

One or more motion sensors may be placed on body part 110. An example of a motion sensor is a low-cost and readily available micro electro-mechanical system (MEMS) inertial measurement unit (IMU). An IMU may contain, for example, tri-axial gyroscopes, accelerometers, and magnetometers. Data streams from one or more IMU may be used to compute angular orientation using data fusion techniques. An IMU may include one or more processor which performs these computations in substantially real time and outputs angular information over a serial communication channel. In the example of FIG. 1A, two IMUs are used: IMU 130 is placed above the knee and IMU 135 is placed below the knee. Electrical signals from IMUs 130 and 135 are provided over signal interfaces 131 and 136, respectively.

In addition to AE sensors and motion sensors, a SEARI system may include other types of sensors. Sensor selection may be application dependent. For example, a sensor that is well-suited to knee and hip applications may be not as well suited for monitoring the integrity of the spinal column. A SEARI system may be designed for a specific application, or may be designed to accommodate flexibility in sensor selection for one or more sensors. A SEARI system may include piezoelectric (PZT) sensors which generate electrical signals in response to physical deformation of a piezoelectric material, and/or electromyography sensors to monitor muscle activity for monitoring of muscle healing or loss of muscle mass due to adverse tissue reaction.

An acquisition interface 140 receives signals from various sensors, such as from AES 120 and IMUs 130 and 135 over signal interfaces 121, 131, and 136, respectively. Acquisition interface 140 may filter, condition, and/or amplify the signals, and prepare the signals for digital signal processing, such as by converting analog signals to digital form, normalizing the digitized signals, and formatting the data into packets if applicable for the processing used. Acquisition interface 140 may store digital representations of the signals in a storage 150 for later access. Storage 150 is volatile or non-volatile memory, discussed in more detail below.

A computing device 160 receives data representing sensor signals from acquisition interface 140, or accesses the data from storage 150, and processes the data to determine a status of natural or artificial joints, the spine, bone, cartilage, or other tissue. Computing device 160 includes at least one processing device, such as one or more of processor, microprocessor, microcontroller, digital signal processor or other microprocessor, application specific integrated circuit (ASIC), and/or field programmable gate array (FPGA), along with associated logic.

Data acquisition in a SEARI system may be performed at high sampling rates. For example, a signal to be sampled may be have signal content of interest at 100 MHz or more, and the sampling rate should be at least the Nyquist rate, or twice the frequency of the signal to be sampled. High-rate analog-to-digital conversion (ADC) units may be included in acquisition interface 140 to enable fast sampling of each channel. Sampling at high rates results in a significant amount of collected data, with corresponding data processing and storage. In some implementations, to offload the data acquisition activity from a main processor, computing device 160 may include a secondary processor dedicated to one or more of data acquisition, data processing, and storage/retrieval activities. A secondary processor may be used to extract a number of valuable metrics from AE data streams such as the number of AE-generating events and their durations, amplitudes, and dominant frequencies. In this way, high data rates that would otherwise make local data processing and storage impractical are reduced by real-time computation of some metrics. A secondary processor may also be used to interface with motion sensors, such that motion sensing can be synchronized with AE data.

Although illustrated as being separate, two or more of acquisition interface 140, storage 150, and computing device 160 may be implemented in one physical electronic device. For example, acquisition interface 140 may include storage 150; computing device 160 may include storage 150; or acquisition interface 140 and storage 150 may be included within computing device 160. Further, although storage 150 is illustrated as being in communication with acquisition interface 140 and computing device 160 over separate interfaces, the actual communication interface may be a single shared bus. In some implementations, computing device 160 receives data from acquisition interface 140 and stores the data to storage 150, and acquisition interface 140 has no access to storage 150. Other implementations are also within the scope of this disclosure.

Figure 1B:
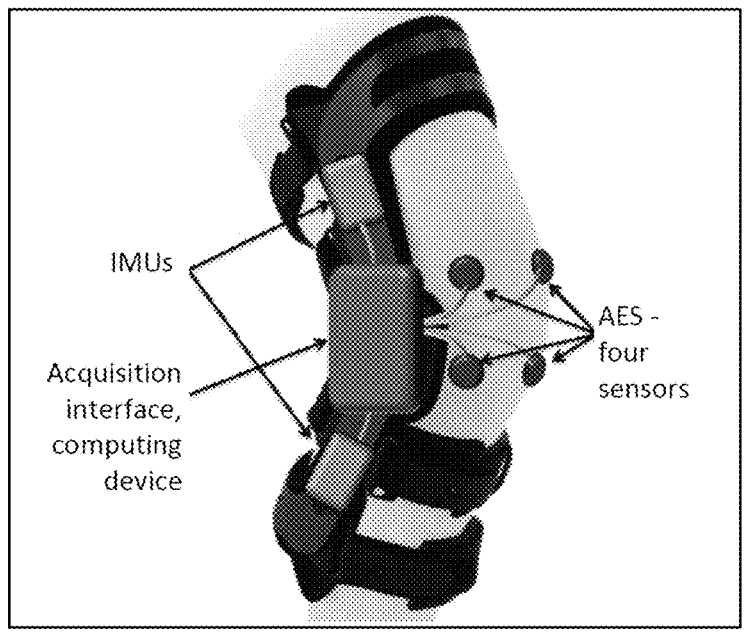
FIG. 1B illustrates an example of a monitoring system implemented as a prosthetic brace.

FIG. 1B illustrates one prototype concept for a physical implementation of a SEARI system for analyzing knee joints using an external prosthetic brace including four acoustic sensors, two IMUs, and a box containing an acquisition interface and a computing device. One embodiment of a SEARI system for knee joints will be described below with respect to the Orthosonos system.

Figure 2:
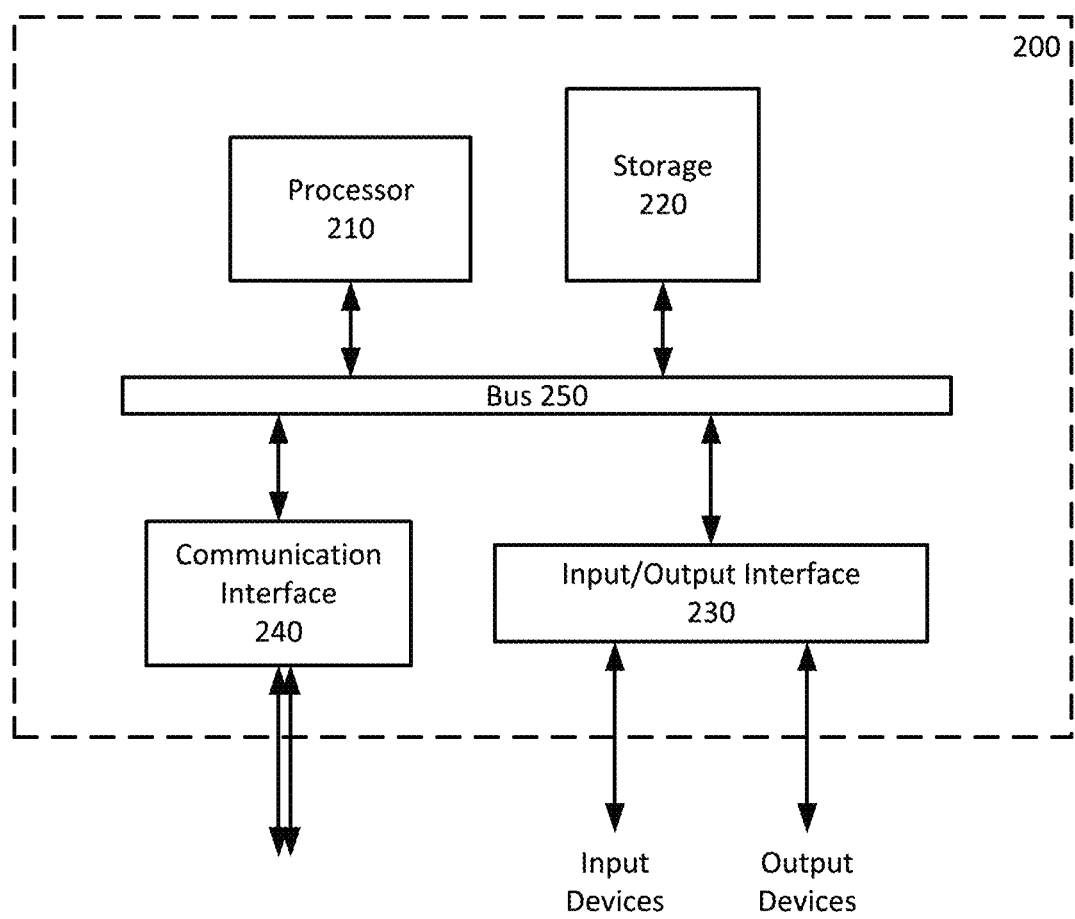
FIG. 2 illustrates an example of a computing device.

FIG. 2 illustrates a general example of a computing device 200 that includes a processor 210, a storage 220, an input/output interface 230, and a communication interface 240. A bus 250 provides a communication path between two or more of the components of computing device 200. The components shown are provided by way of illustration and are not limiting. Computing device 200 may have additional or fewer components, or multiple of the same component.

Processor 210 represents one or more of a processor, microprocessor, digital signal processor, microcontroller, application specific integrated circuit (ASIC), and/or field programmable gate array (FPGA), along with associated logic.

Storage 220 represents one or both of volatile and non-volatile memory for storing information. Examples of memory include semiconductor memory devices such as EPROM, EEPROM and flash memory devices, magnetic disks such as internal hard disks or removable disks, magneto-optical disks, CD-ROM and DVD-ROM disks, and the like.

Portions of the SEARI system may be implemented as computer-readable instructions in storage 220 of computing device 200, executed by processor 210. While processor 210 is executing the instructions from storage 220, computing device 200 is transformed into a special-purpose computer.

An embodiment of the SEARI system includes a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits ("ASICs"), programmable logic devices ("PLDs"), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

Input/output interface 230 represents electrical components and optional code that together provides an interface from the internal components of computing device 200 to external components. Examples include a driver integrated circuit with associated programming Acquisition interface 140 of FIG. 1A may be implemented in input/output interface 230.

Communication interface 240 represents electrical components and optional code that together provide an interface from the internal components of computing device 200 to external devices and/or networks. Communication interface 240 may include wired or wireless interfaces, or a combination of wired and wireless interfaces.

A SEARI system may include the capability of wirelessly networking with other SEARI systems via communication interface 240, as a subject might wear a number of SEARI systems at the same time. For example, aspects of gait and motion may be monitored during rehabilitation following a knee implant, but monitoring the repaired joint by itself may be insufficient to detect uneven gait resulting from favoring one or the other knee. In this case, the subject might wear one SEARI system on each knee and another on the torso.

A SEARI system may include networked processors to enable body area networking and data offloading. To synchronize and interpret data from multiple SEARI systems and other devices, a body area network may be implemented. In a body area network, each SEARI system on the body may be a node, which is a slave to a central master controller. The master may be implemented on one of the nodes, or may be implemented on a device within the network, such as a smart phone or tablet. The master controller may provide a graphical user interface and may store sensor data. If the master controller includes a graphical user interface, sensor data or fused data may be presented in a visual manner. Data may be stored or presented visually in substantially real time. The master controller may further have the capability to forward or directly save sensor data or fused data to server storage via communication interface 240.

Bus 250 represents one or more interfaces between components within computing device 200. For example, bus 250 may include a dedicated connection between processor 210 and storage 220 as well as a shared connection between processor 210 and multiple other components of computing device 110.

Computing device 160 of FIG. 1 may be implemented using a device such as computing device 200 or similar device to monitor status of joints, spine, cartilage, and other tissue, such as monitoring for wear, damage, or progress.

Figure 3:
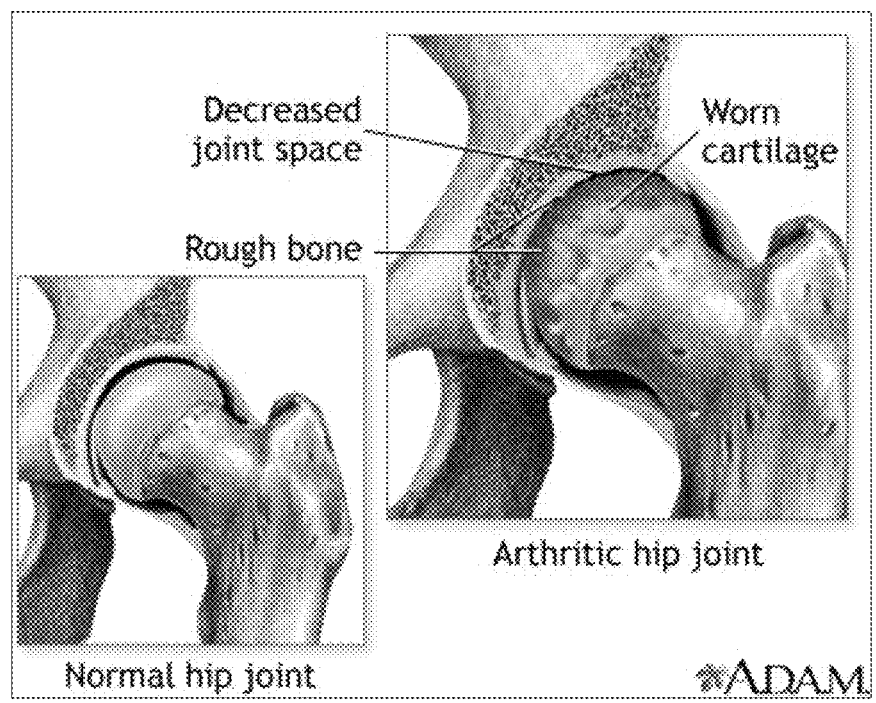
FIG. 3 illustrates a source of acoustic emission.
Figure 4:
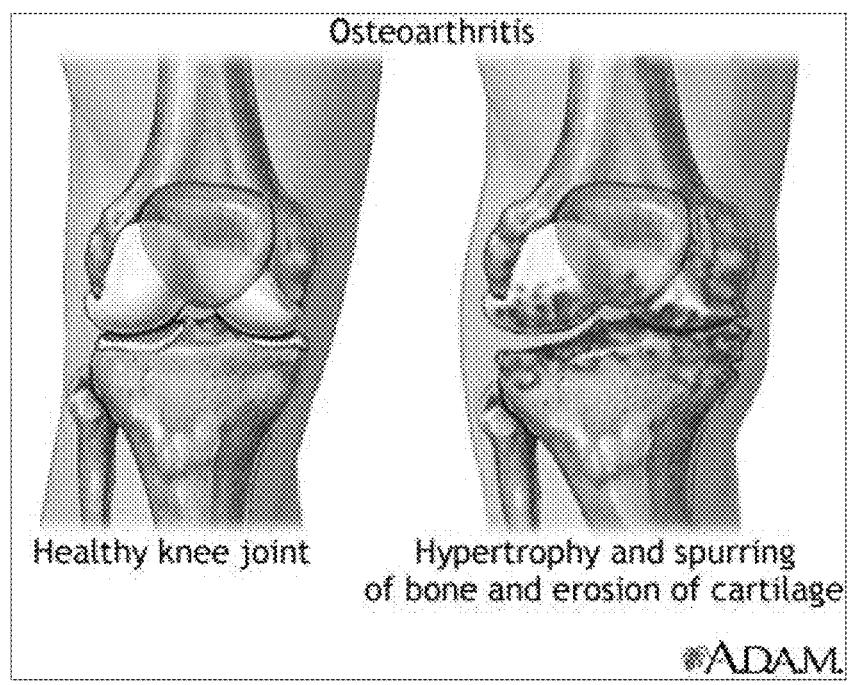
FIG. 4 illustrates an example of measurement of acoustic emission.
Figure 5:
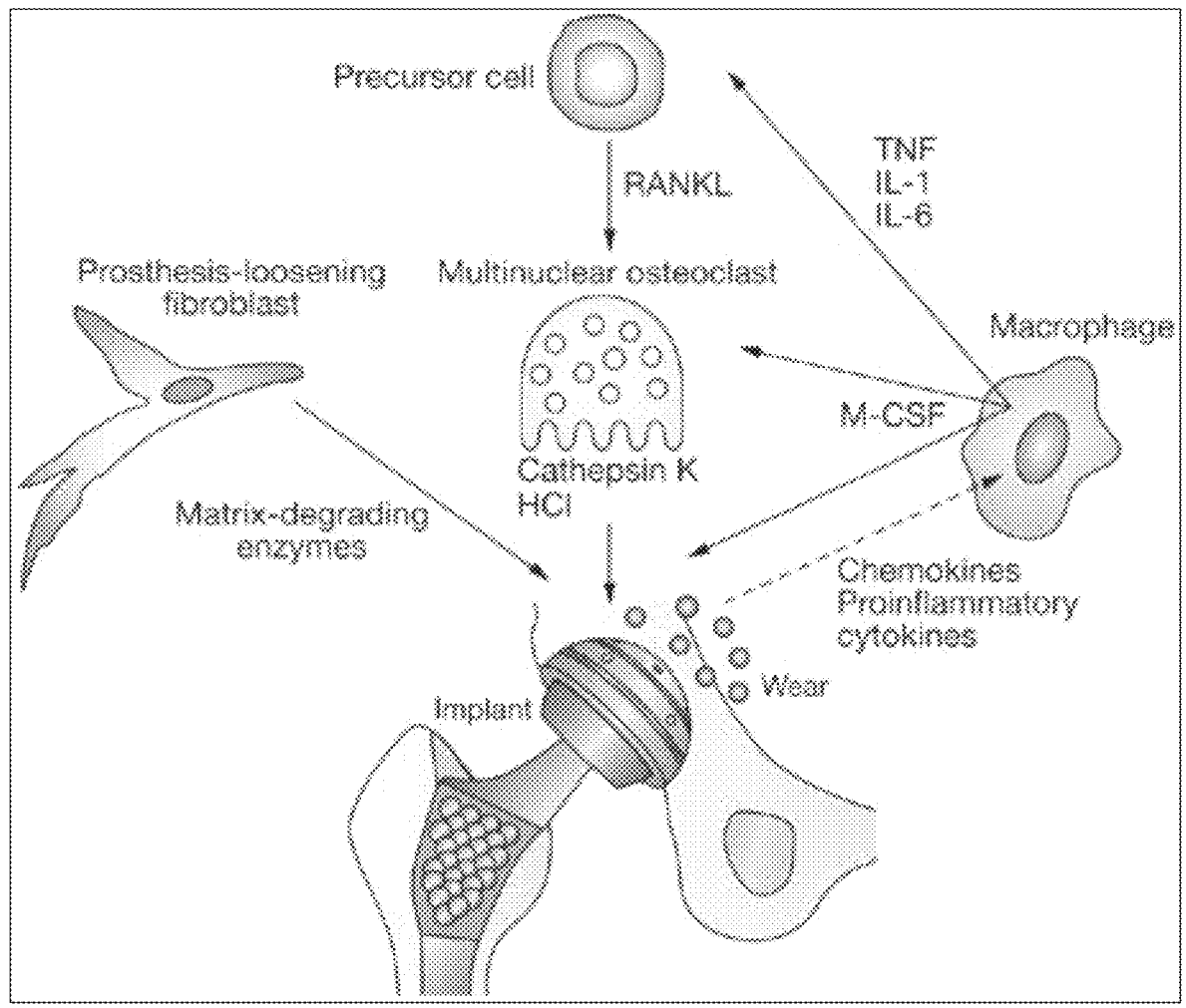
FIG. 5 illustrates an example of hip joint cartilage wear.

FIGS. 3-5 are presented for better understanding of some types of joint wear and damage. FIG. 3 illustrates one type of damage that may occur to a hip joint; FIG. 4 illustrates one type of damage that may occur to a knee joint; and FIG. 5 illustrates an implanted joint in which wear debris induces interplay between prosthesis-loosening fibroblasts, multinucleated osteoclasts and macrophages.

Figure 6:
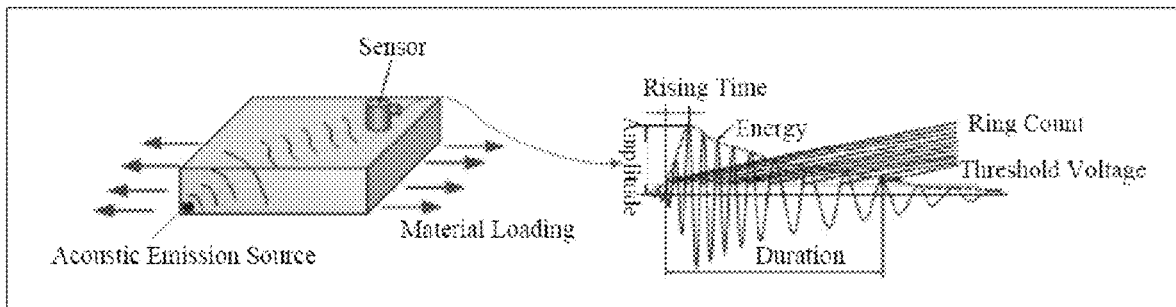
FIG. 6 illustrates an example of knee joint wear.

AE is used to monitor a wide array of phenomena including dislocation propagation, fracture initiation and propagation, elasto-plastic deformation, corrosion, wear, and fatigue. As a patient moves, AE may be monitored. AE may be a sound wave resulting from a sudden release of strain energy, known as a stress wave, that propagates through a material and may be measured. FIG. 6 illustrates the concept generally for a material that is loaded until failure, at which point the material breaks in some fashion, generating AE. In a human body, an AE source may be, for example, joint surfaces rubbing against one another, and the generated AE may be detected.

Figure 7:
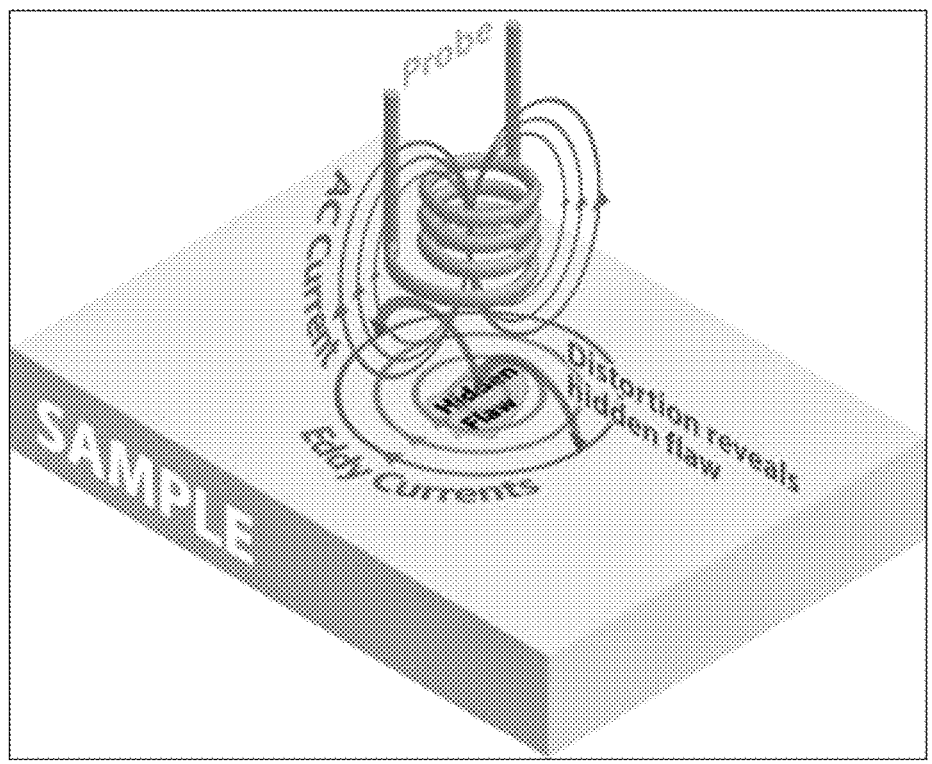
FIG. 7 illustrates an example of wear in an artificial joint.

AE may be measured by listening to the sound emission directly, or by listening to how a generated sound is varied during transmission within a material. The latter may be accomplished using electromagnetically-induced AE (EMAE). The general concept of detecting a defect in a material using EMAE is illustrated in FIG. 7. An electromagnetic field generates eddy currents in a material, which are distorted around a defect in the material. The distortion may be detected and used to locate and identify the defect. In a SEARI system, an electromagnetic field may be applied to an area which induces eddy currents from, for example, a conductive implant such as a brace, plate, screw, or nail. The eddy currents propagate through the body area, and are modified as they pass through different materials of the body. The eddy currents are received and may be used to locate and detect areas of concern around the implant. EMAE may be detected with conventional AE sensors and/or special fiber optic (FO) sensor networks.

The characteristics of AE, such as frequency, amplitude, duration, growth rate and decay rate, are a function of the properties of the material in which the AE is generated. These AE characteristics are recognizable out of other acoustic signals generated by the surrounding environment. For example, AE frequencies for wear may be orders of magnitude higher than muscle, skin or bone natural vibration frequencies. Additionally, there may be AE differences between healthy and damaged body parts, between similar damage in different parts of the body, and between different types of damage in the same body part. Studies have shown, for example, that there are differences in AE between young healthy knees and older osteo-arthritic knees, that there is a correlation between changes in a knee AE profile and the progression of joint aging and degeneration, that there are differences in AE between failures of different spinal components in dynamic loading in vitro, and that AE from compressive fractures are associated with higher amplitudes and frequencies than tensile failures.

Acoustic signals may be compared against known AE profiles. For example, a generic AE profile of a knee may be created based on one or more measurements of healthy knee AE, and the AE of a patient's knee may be compared to the generic profile for identification of possible adverse knee conditions. For another example, a baseline of a patient's bone AE after fixation surgery may be stored as a baseline, and subsequent AE may be compared to the baseline for monitoring the healing process. For yet another example, AE of a joint may be compared to a stored AE representative of a known condition to determine if the patient is likely to have that condition.

A SEARI system thus includes the ability to contextualize AE measurements by synchronizing acoustic sensing and motion sensing capabilities, providing the ability to monitor joint, spine, bone, cartilage, and other tissue health continuously over long periods, and during a patient's daily activities.

A SEARI system may be used in combination with one or more motion models. A motion model may include a sequence of motions that have been identified as producing AE indicative of one or more health conditions. A motion sequence may be, for example, walking, climbing up or down a stair, standing from a sitting position, sitting from a standing position, lifting of a weight, or pulling against a resistance band. A patient may be requested to follow the motion sequence while generated AE is monitored, and the generated AE compared with known AE indicative of a health condition. Alternatively, the patient may be monitored by the SEARI system during daily activities: information from motion, angle, position, velocity, acceleration, pressure, and/or other sensors may be interpreted to determine when a particular motion sequence has occurred, then AE received during the detected motion sequence may be analyzed to determine if they correlate to one or more AE sequences indicative of a health condition.

Having generally described a SEARI system, one implementation will next be described in detail with respect to a joint monitoring system referred to herein as Orthosonos, which uses a sensing system that emphasizes high frequencies to reduce interference from environmental acoustic noise or noise associated with AE of sensor attachment systems. Sampling bandwidth may be high, requiring rapid sample accumulation, such as mega-samples-per-second (Msps); and observation periods may be lengthy, such as in terms of minutes, requiring high storage capacity. The combination of requirements for rapid sample accumulation and high storage capacity may make a conventional solution impractical and costly, and more practical conventional solutions are prone to data loss under high performance sampling conditions. Triggered sampling is used to acquire signals that exceed background noise level (e.g., exceeds twice the root-mean-square (RMS) amplitude of the noise), which minimizes data loss of high performance sampling.

Figure 10:
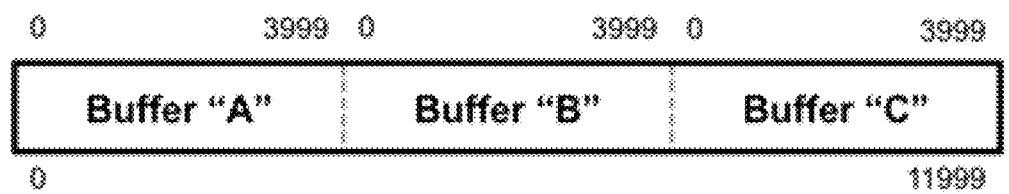
FIG. 10 illustrates an example of data buffering.

Alternatively or additional to triggered sampling, a standard deviation threshold technique may be used, in which acoustic sensor samples are acquired continuously (i.e., at the sample rate, such as at 1 Msps). If triggered sampling is used additionally, the signals are acquired continuously while the signal amplitude exceeds the threshold. In the standard deviation threshold technique, the signal samples are buffered in a series of 4000-element buffers. FIG. 10 is illustrative, showing three buffers A, B, and C with beginning and ending indexes (0 to 3999 for a total of 4000 elements) of each buffer along the top, and the time in microseconds along the bottom for a 1 Msps sample rate. The AE signal samples are stored with a time stamp. When a buffer is detected as being filled, the standard deviation of the samples in the buffer is calculated and compared to a threshold. The threshold may be set in memory, set at manufacturing, set during configuration, or set based on present or expected noise levels.

If the standard deviation of the samples in a buffer is greater than the threshold, the buffer and neighboring buffers are saved as one event. Thus, if the standard deviation of the samples in buffer B in the example of FIG. 10 is greater than the threshold, buffers A-C are saved as one 12,000 sample event, and if the samples in buffer A also have a standard deviation greater than the threshold, it will be saved along with its adjacent neighbor buffers (including buffer B and the buffer immediately preceding buffer A in time) as a separate event. Similarly, if the standard deviation of the samples in buffer C exceeds the threshold, buffer C will be saved as the center of a three-buffer sequence (starting with buffer B) as another and separate event.

Each saved sample event buffer set is searched to find the time where high-variance periods occur. These high-variance instances are saved for further examination and classification. Because buffer contents may appear in multiple events, redundant data is identified by examining buffer content time stamp values, and redundant data is removed.

Orthosonos monitors joints, and analyzes signals to identify phenomena associated with classifications of tribological properties. Tribology relates to surfaces in relative motion, including friction and wear of the surfaces, and including lubrication to reduce friction and wear. Tribology principles indicate that AE may be analyzed to characterize the state of surfaces operating as bearing surfaces. Examples relevant to Orthosonos are prosthetic knee and hip implant structures with relative motion of surfaces that may be lubricated by synovial fluid. Orthosonos senses AE to use in the detection of structure health for structures internal to the body, including original and prosthetic structures.

As a result of wear, surface roughness profiles including asperities may form. For smooth surfaces that have been prepared and have not been exposed to long term operation and wear, friction results from stick-slip events. After the onset of roughness, in addition to the stick-slip events, collisions of surface roughness features during relative surface motion occur, resulting in further wear, microscopic fracture at surfaces, and the formation of debris at bearing surfaces.

The relative motion of surfaces, stick-slip events, and collision of surface roughness features results in force being applied to the surfaces. The forces are short-duration impulses (e.g., 10 to 1000 microseconds) which induce vibration in the structure and surrounding materials. The resulting acoustic signal includes both vibrational modes of the structure and compressional waves in the surrounding materials (e.g., prosthetic joint materials). The impulses vary markedly for smooth or rough surfaces.

Figure 8:
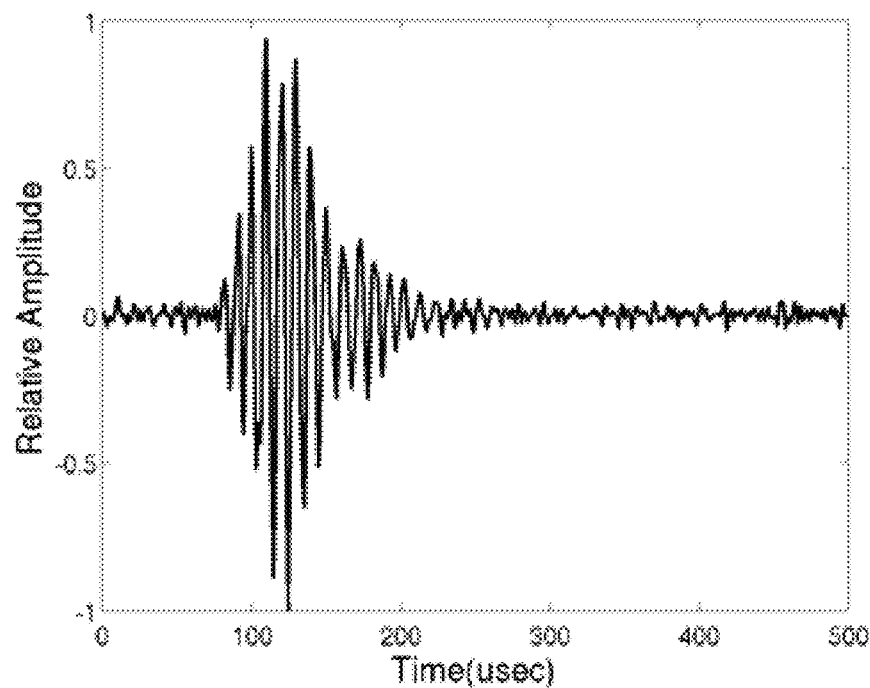
FIG. 8 illustrates an example of an acoustic event of a smooth surface.
Figure 9:
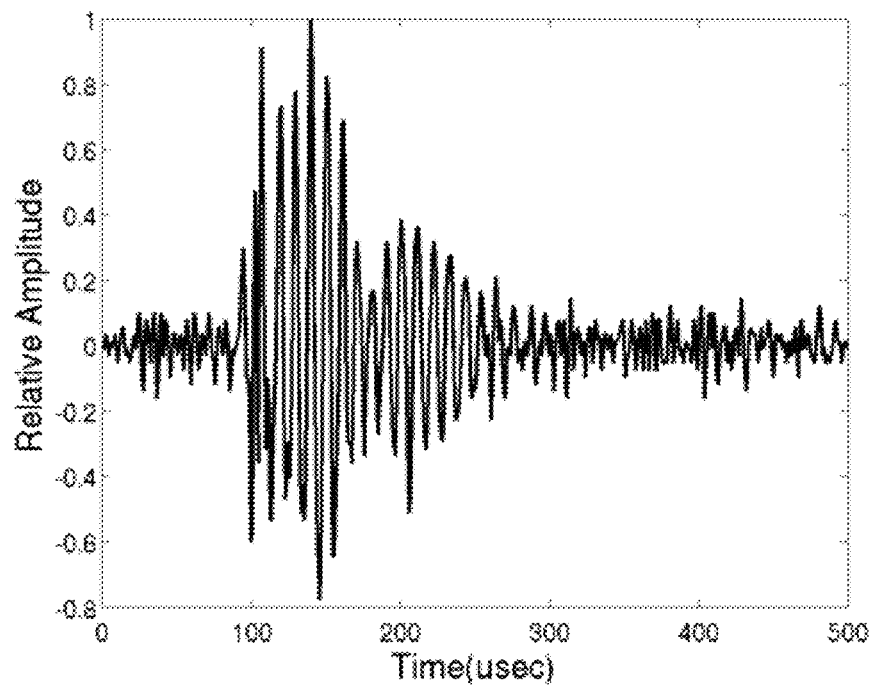
FIG. 9 illustrates an example of an acoustic event of a worn surface.

For example, new implants with as-manufactured smooth surfaces will produce emissions consistent with smooth surface tribological stick-slip events caused by two smooth surfaces moving against each other under pressure. As the two surfaces move, their motion is impeded by a sequence of bond and disbond events resulting in a single emission characterized by a sharply rising signal followed by an exponential decay. An example of such an emission is shown in FIG. 8. In contrast, worn surfaces of fatigued implants may have large scale imperfections. As a moving surface encounters such an imperfection, a series of emissions occurs. The resulting emission is quite different from the smooth-surface emission. A complex envelope shape may be evident, and the decay of ringing waves will not exhibit exponential decay behavior. An example of such an emission is shown in FIG. 9. Thus, the Orthosonos AE signal classification includes distinguishing between single impulse events (SIE) and compound impulse events (CIE).

The signal samples are analyzed in the time domain Conventional frequency-domain signal classification is not sufficient for classification of joint wear state signals, as a result both of the short time duration impulse characteristics of the signals as well as the influence of frequency characteristics on spatial location of events. Classification includes techniques for angle-resolved classification, attenuation insensitive classification, and transparent unbiased classification—angle-resolved classification uses motion measurement and time synchronization to enable classification techniques to be restricted to motion where the largest joint forces appear; attenuation insensitive classification allows classification even as signal attenuation varies, such as may occur depending on tissue characteristics near the joint site and in the region underlying the applied sensor system, providing a robust classification as signal attenuation (and correspondingly, amplitude) varies; a transparent and unbiased classification is a hierarchical cluster technique that provides transparency regarding signal characteristics that contribute to classification, and requires no preliminary bias in selection.

Figure 11:
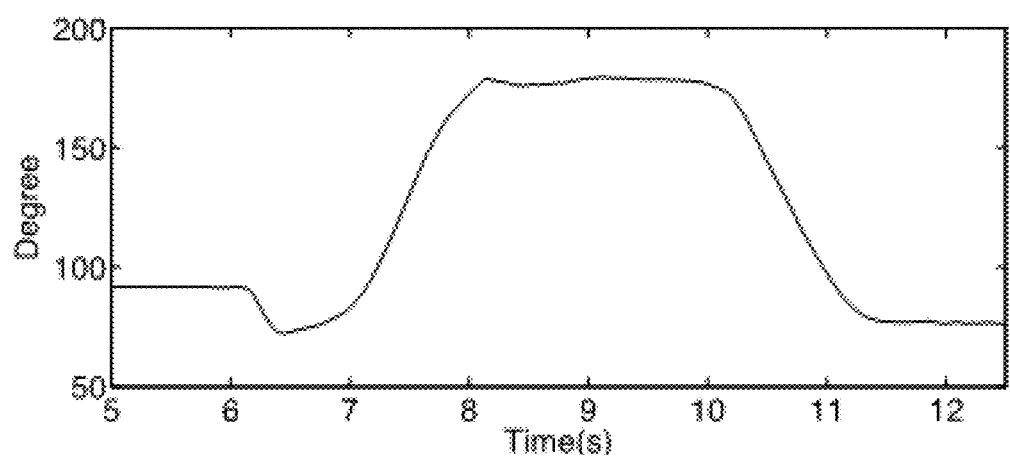
FIG. 11 illustrates an example of measured angular movement.

Angle-resolved classification uses joint angle measurement based on sampling of signals from inertial sensors. For example, inertial sensors may be placed at the tibial crest and at the femur above the knee. During a sit-to-stand maneuver, the joint angle changes from approximately 90 degrees in a seated position to approximately 180 degrees in a standing position, and the inverse for returning to a seated position. FIG. 11 is illustrative. Note that as the subject prepares to stand, the legs may move to support the standing motion, and the leg movement may be more pronounced when the legs are initially extended in front of the seat or pulled in under the seat. Such leg movement results in a change of joint angle, such as is illustrated in FIG. 11 within the 6-7 second portion of the time axis.

As noted above, Orthosonos discriminates between SIE and CIE events. Orthosonos further discriminates between details of event characteristics. SIE, CIE, and other events exhibit time-dependent profiles. These profiles are referred to herein as Event Envelopes.

Figure 12:
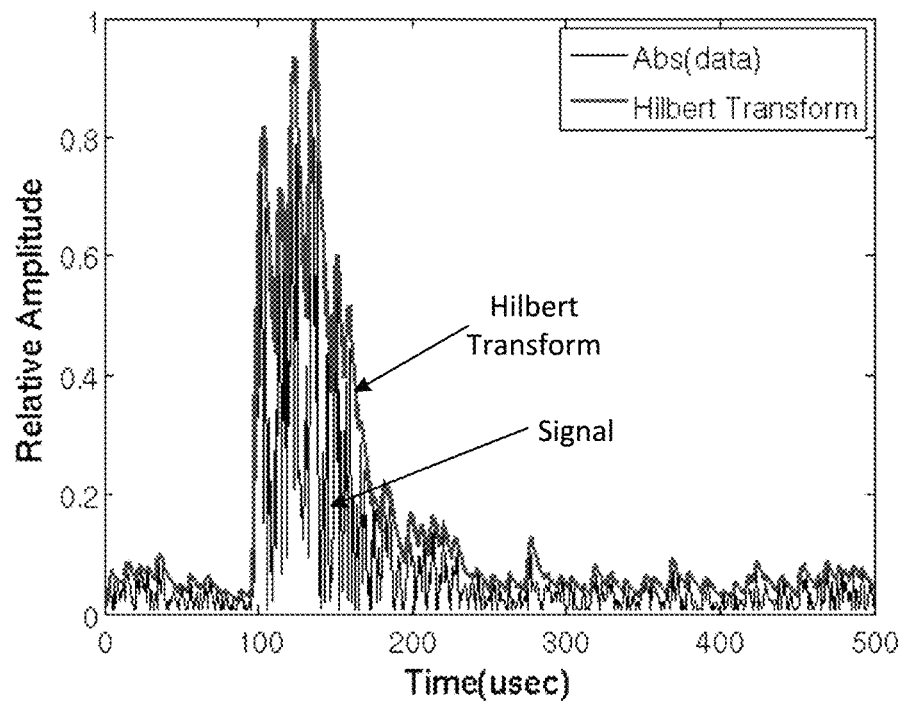
FIG. 12 illustrates an example of a signal and its Hilbert Transform for an acoustic event.

An Event Envelope determination technique is based on the Hilbert transform. One of the properties of this transform enables it to be used as a demodulator for amplitude modulated signals. Determination of an Event Envelope begins with computation of a complex signal with two components: the real part being the signal s(t), and the imaginary part being the Hilbert Transform of this signal ŝ(t). FIG. 12 is illustrative, in which the Hilbert transform ŝ(t) of an event is plotted along with the absolute value of the associated signal s(t). The Event Envelope x(t) of a signal s(t) is the magnitude of the complex signal, as shown in Equation 1.

$$x(t) = \sqrt{s(t)^2 + \hat{s}(t)^2} \quad (1)$$

Figure 13:
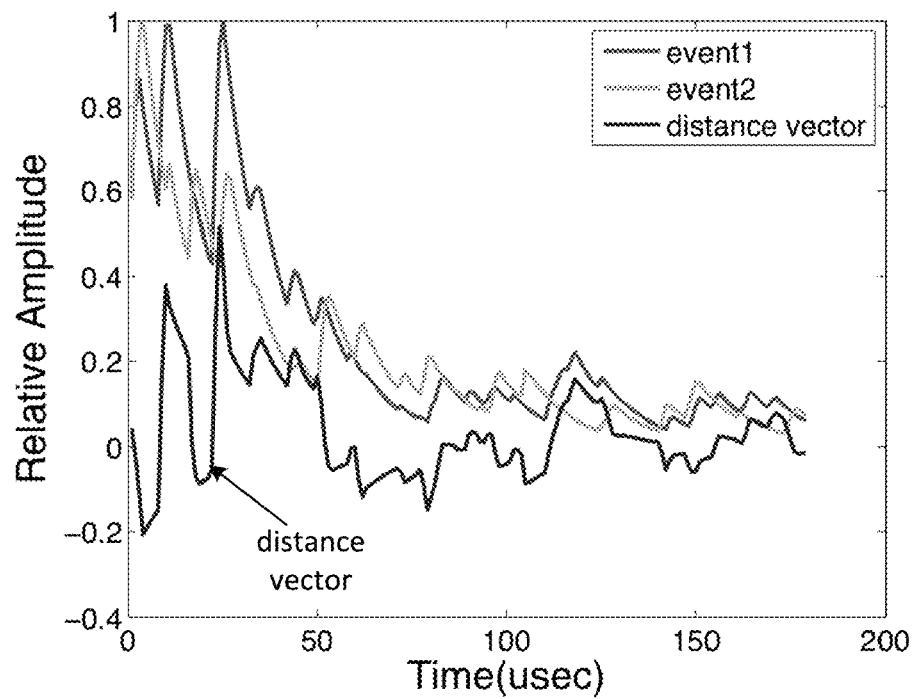
FIG. 13 illustrates an example of two acoustic events and their relative distance to each other.

Orthosonos signal classification includes a determination of differences between Event Envelopes, by identifying feature vectors that measure the amplitude of an Event Envelope. An Event Envelope feature vector includes N vector elements corresponding to 'n' samples of the Event Envelope. A feature vector of an Event Envelope x(t) is referred to as x(k). In the feature vector, amplitudes are normalized, with the maximum signal amplitude assigned to unity. Normalization provides amplitude independence and thus substantial immunity to variable attenuation. The feature vectors are aligned to synchronize their starting points. FIG. 13 illustrates the profiles of two feature vectors, along with a profile representing the difference between the two feature vectors. For convenience, the profile of a feature vector x(k) is referred to as the x(k) envelope.

An increase in the x(k) envelope is indicative of the presence of AE. On the other hand, a decrease in x(k) envelope might result from the superposition of two or more signals with different frequency elements changing phase relative to one another, and such a decrease is therefore not necessarily indicative of a dissipating signal. Due to the potentially large differences between two similar AE events that may result from an artifact associated with a rapid variation in x(k) envelope as it follows individual wave periods, a one-way low-pass filter may be applied to x(k). The resulting filtered y(k) envelope increases with an increase in the x(k) envelope without attenuation, but decreases subject to single pole infinite impulse response (IIR) low pass filter characteristics, as shown in Equation 2.

$$y(k) = \max[x(k), \alpha y(k-1)] \quad (2)$$

where $0<\alpha<1$ determines the time constant of the low-pass filter while ensuring that the rate of signal decay not exceed the time constant of the system.

The Euclidean distance between two envelopes $x_i(k)$ and $x_j(k)$ (or $y_i(k)$ and $y_j(k)$) is computed as the vector distance between each of the N feature vector elements. The Euclidean distance is defined in Equation 3.

$$d(x_i, x_j) = \sqrt{\sum_{k=1}^{N}(x_{i,k} - x_{j,k})^2} \quad (3)$$

Techniques appropriate for signal classification are preferably flexible, unbiased, and matched to the requirements for systematically evaluating similarities and differences between event types. Accordingly, a clustering technique is one technique suitable for the concepts in this disclosure. A hierarchical clustering technique is flexible to accommodate variations in the diversity of event types and their populations, and uses unsupervised learning.

Hierarchical clustering begins with the creation of an N×N matrix where each matrix element for indices i and j is equal to the distance $d(x_i, x_j)$ between the vectors $x_i$ and $x_j$. The matrix is symmetric (i.e., $d(x_i, x_j)=d(x_j, x_i)$) and has a zero diagonal because $d(x_i, x_j)=0$. Thus, a lower triangle matrix is apparent in the N×N matrix, and the lower triangle is used for clustering.

Each column of the N×N matrix represents an elementary cluster. New clusters are formed from the N×N matrix using the Unweighted Pair Group Method with Arithmetic Mean (UPGMA) technique, based on separation between clusters. Separation $d_{a,b}$ for two clusters, 'a' and 'b' is the average of all distances between members of two clusters, as shown in Equation 4.

$$d_{a,b} = \frac{1}{|A||B|} \sum_{a \in A} \sum_{b \in B} d(a, b) \quad (4)$$

The UPGMA technique creates a hierarchical tree structure, as illustrated by way of FIGS. 14A-I for feature vectors A-E. A lower triangle matrix is populated (FIG. 14A) with the distance between each two vectors. The shortest distance in the matrix is used to determine a new cluster. In FIG. 14A, the shortest distance is between feature vectors A and B (the number 2 in the matrix element at the intersection of column A, row B is the smallest). Feature vectors A and B thus are used to form new cluster AB. Matrix rows and columns for A and B are replaced with a single row and column for new cluster AB (FIG. 14B) containing values determined by equation 4. Clustering continues (in this example) with the next smallest distance (the element at the intersection of column D and row E), replacing the rows and columns for D and E with a single row and column for cluster DE combined (FIG. 14C) containing a value determined by equation 4. The next smallest distance is the element at the intersection of column AB and row C, thus AB and C are clustered as ABC (FIG. 14D). Thus, after clustering, elementary clusters A, B, C, D, and E are joined by new clusters AB, ABC, and DE.

FIG. 14 also illustrates a corresponding dendrogram construction sequence, resulting in a hierarchical binary tree: FIG. 14E illustrates elementary clustering; FIG. 14F illustrates the AB cluster; FIG. 14G illustrates the AB cluster and the DE cluster; FIG. 14H illustrates the ABC cluster and the DE cluster, and FIG. 14I illustrates the resultant full binary tree of six leaf nodes.

The cluster dendrogram provides capability for classification. Event Silhouettes corresponding to the geometric mean of each cluster may be computed, and an AE event may be associated with a cluster based on a computation of Euclidean distances between the feature vector envelope and each of the Event Silhouettes.

Determination of Event Silhouettes for each cluster is performed using an iterative k-means technique. For each cluster with N feature vector elements $(x_1, x_2, \ldots, x_N)$, the k-means determination of the Event Silhouette for the cluster produces an Event Envelope Descriptor, $\mu$, such that $\mu$ minimizes the sum of distance squares D, defined in Equation 5.

$$D = \sum_{i=1}^{N} |x_i - \mu_i|^2 \qquad (5)$$

Figure 15:
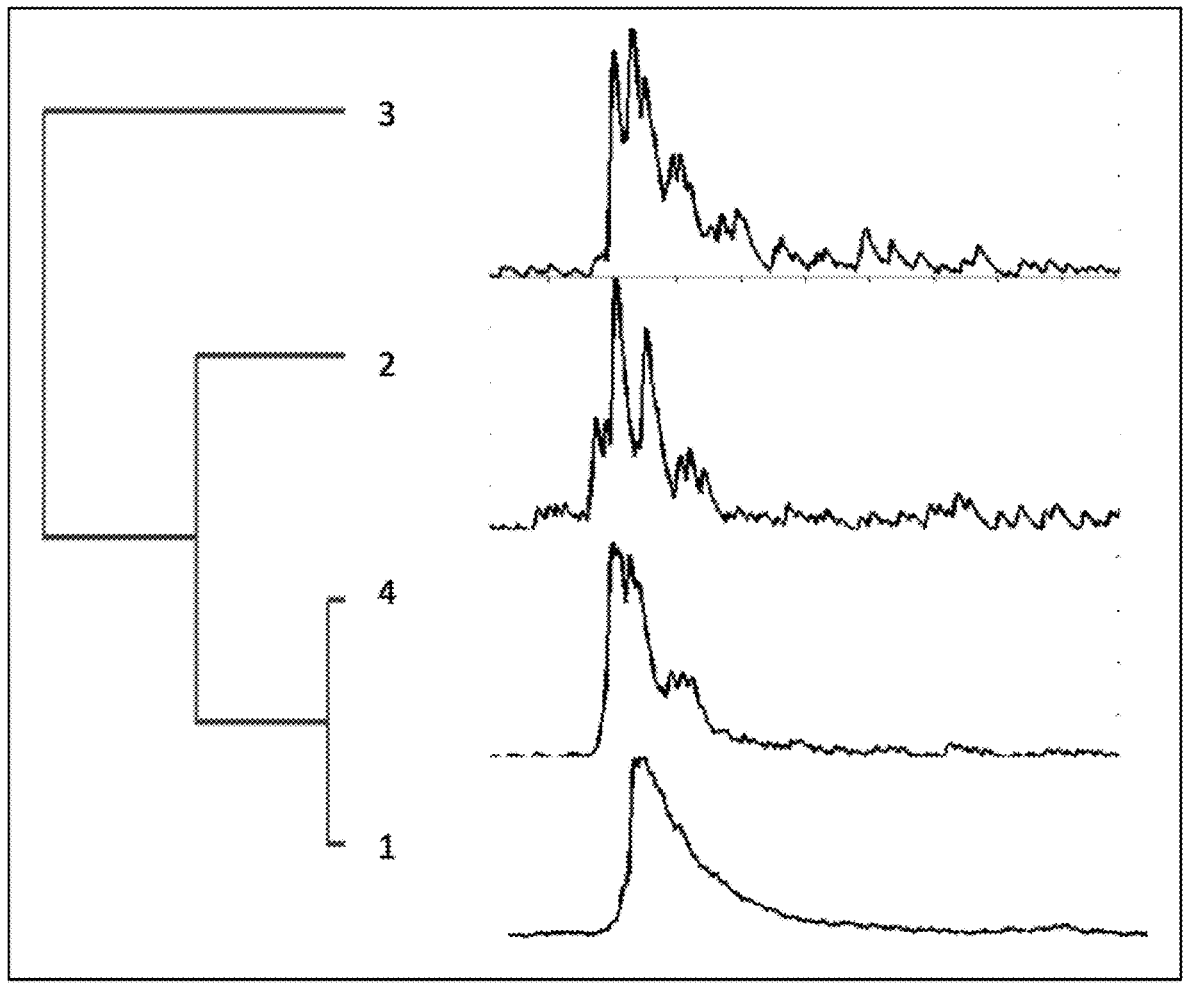
FIG. 15 illustrates an example of a dendrogram and corresponding event silhouettes.

FIG. 15 illustrates an example of a dendrogram and corresponding Event Silhouettes for left knee (two-week post-operation prosthetic) and right knee (12-year post-operation prosthetic) AE measurements of a subject.

The hierarchical cluster system is used to compare an acquired Event Envelope feature vector with available Event Silhouettes. Assignment of an Event Envelope as a member of a set S of k clusters corresponds to finding the cluster for which the distance between the Event Envelope feature vector x(k) and an Event Silhouette is a minimum—finding the Event Silhouette $\mu_j$ that minimizes the sum of distance squares for the $j^{th}$ cluster $D_j$, defined in Equation 6.

$$D_j = \arg\min_{1 \le j \le k} \sum_{i=1}^{N} |x_i - \mu_{j,i}|^2 \qquad (6)$$

Because the clustering technique distributes events into respective clusters, the relative population of events in clusters is expected to indicate the relative occurrence of these events. Metrics may be determined based on the relative occurrence of events. Such metrics may be ratiometric, rather than being an absolute value, thereby reducing the sensitivity of metric determination to phenomena that may provide variance in event occurrence independent of joint state. A demonstration showing the technique effectiveness in making proper discrimination between events was performed for four metrics. The metrics were used for discrimination between Fatigued implants and those classified as Recent or Functional. Fatigued implants are those with greater than 10 years of use. Recent or Functional implants are those implants with less than or equal to 5 years of use. Each metric included an offset value of unity to ensure finite value of the metric in the absence of events.

1. Metric 1: The ratio of events in Cluster 1 with the sum of events in Cluster 3.
2. Metric 2: The ratio of events in Cluster 1 with the sum of events in Clusters 2 and 3.
3. Metric 3: The ratio of the sum of events in Clusters 1 and 4 with the sum of events in Clusters 3.
4. Metric 4: The ratio of the sum of events in Clusters 1 and 4 with the sum of events in Clusters 2 and 3.

The population of events for right and left knee prosthetics used for determining metrics 1-4 is shown in Table 1.

TABLE 1

| Subject ID | Knee | Prosthetic State | Cluster1 | Cluster2 | Cluster3 | Cluster4 |
|---|---|---|---|---|---|---|
| 1022 | right | Recent | 4 | 0 | 0 | 0 |
| 1025 | left | Recent | 4 | 0 | 2 | 4 |
| 1025 | right | Recent | 10 | 0 | 2 | 5 |
| 1029 | left | Functional | 30 | 3 | 4 | 21 |
| 1029 | right | Functional | 9 | 0 | 2 | 10 |
| 1020 | right | Fatigued | 43 | 1 | 1 | 4 |
| 1020 | left | Recent | 14 | 1 | 4 | 2 |
| 1030 | right | Fatigued | 33 | 1 | 3 | 24 |

Figure 16:
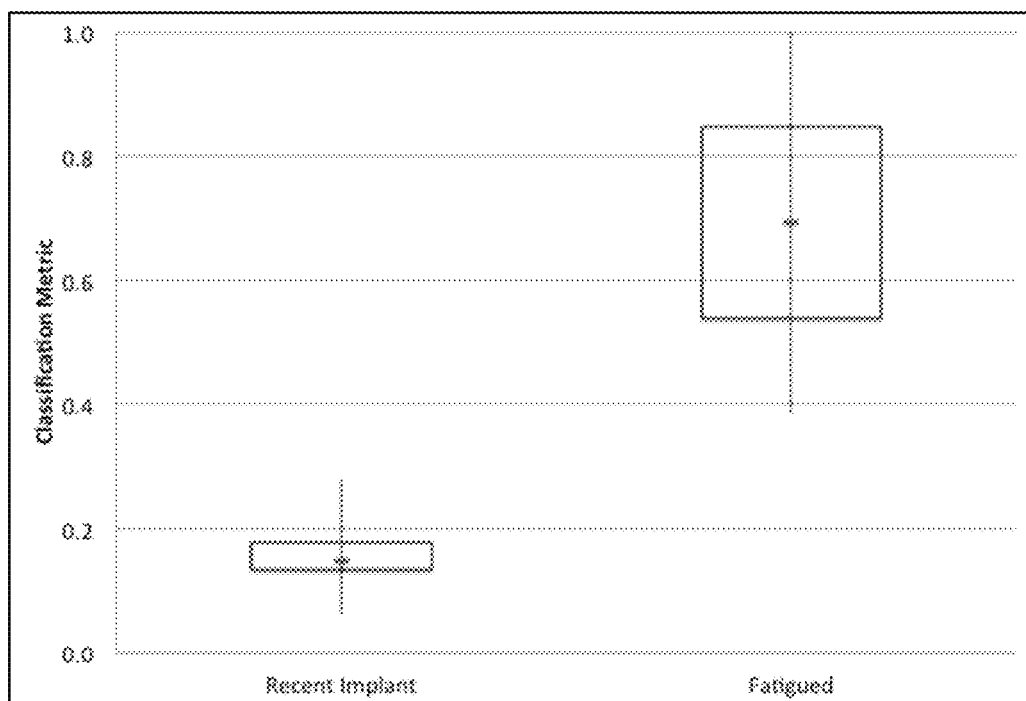
FIGS. 16-19 illustrate examples of "box and whisker" plots of cluster data.

The results for Metric 1 (ratio of events in Cluster 1 with the sum of events in Cluster 3, offset of unity) are shown in Table 2. FIG. 16 illustrates a "box and whisker" plot of the data in Table 2. Metric 1 shows clear discrimination between Fatigued state and Recent and Functional state of the implants.

TABLE 2

Metric 1, Results
Ratiometric Metric Values

| Recent and Functional State | | Fatigued State | |
|---|---|---|---|
| Subject ID | Value | Subject ID | Value |
| 1020 Left | 2.8 | 1029 Right | 21.5 |
| 1022 Right | 4.0 | 1030 Right | 8.3 |
| 1025 Left | 1.3 | | |
| 1025 Right | 3.3 | | |
| 1029 Left | 6.0 | | |
| 1029 Right | 3.0 | | |

Figure 17:
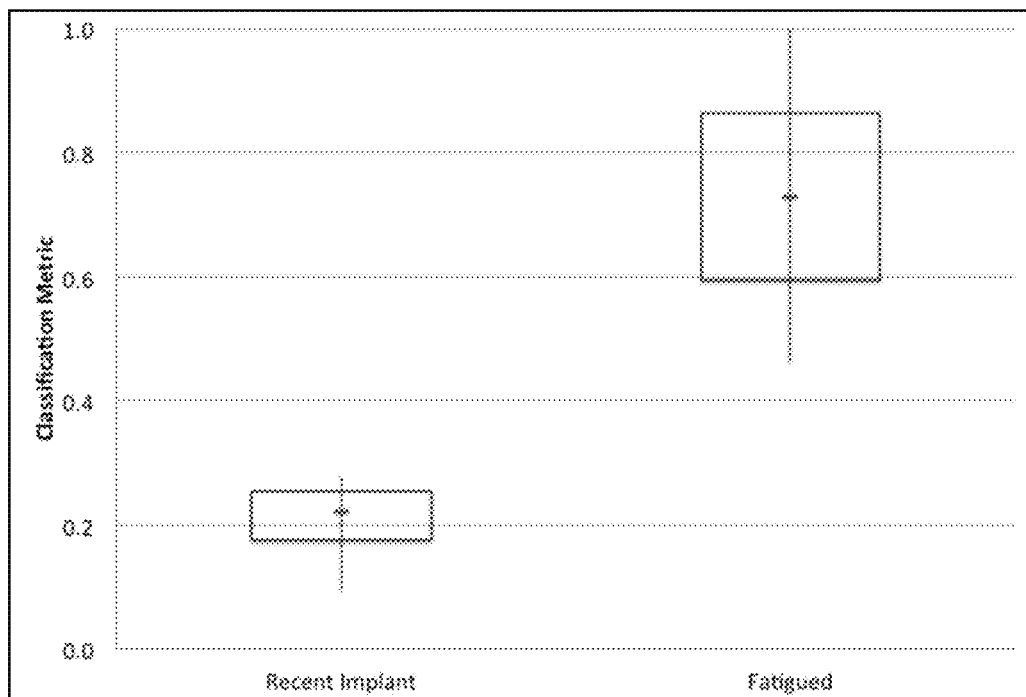

The results for Metric 2 (ratio of events in Cluster 1 with the sum of events in Clusters 2 and 3, offset of unity) are shown in Table 3. FIG. 17 illustrates a "box and whisker" plot of the data in Table 3. Metric 2 also shows clear discrimination between Fatigued state and Recent and Functional state of the implants.

TABLE 3

Metric 2, Results
Ratiometric Metric Values

| Recent and Functional State | | Fatigued State | |
|---|---|---|---|
| Subject ID | Value | Subject ID | Value |
| 1020 Left | 2.3 | 1029 Right | 14.3 |
| 1022 Right | 4.0 | 1030 Right | 6.6 |
| 1025 Left | 1.3 | | |
| 1025 Right | 3.3 | | |
| 1029 Left | 3.8 | | |
| 1029 Right | 3.0 | | |

Figure 18:
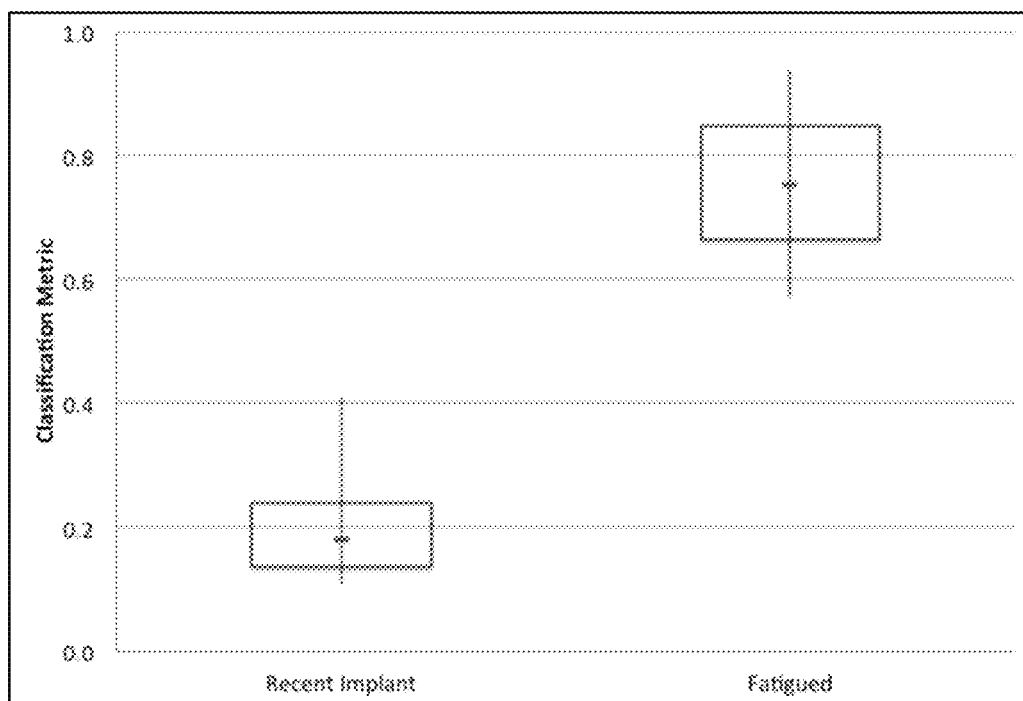

The results for Metric 3 (ratio of the sum of events in Clusters 1 and 4 with the sum of events in Cluster 3, offset of unity) are shown in Table 4. FIG. 18 illustrates a "box and whisker" plot of the data in Table 4. Metric 3 also shows clear discrimination between Fatigued state and Recent and Functional state of the implants.

TABLE 4

Metric 3, Results
Ratiometric Metric Values

| Recent and Functional State | | Fatigued State | |
|---|---|---|---|
| Subject ID | Value | Subject ID | Value |
| 1020 Left | 3.2 | 1029 Right | 23.5 |
| 1022 Right | 4.0 | 1030 Right | 14.3 |
| 1025 Left | 2.7 | | |
| 1025 Right | 5.0 | | |
| 1029 Left | 10.2 | | |
| 1029 Right | 6.3 | | |

Figure 19:
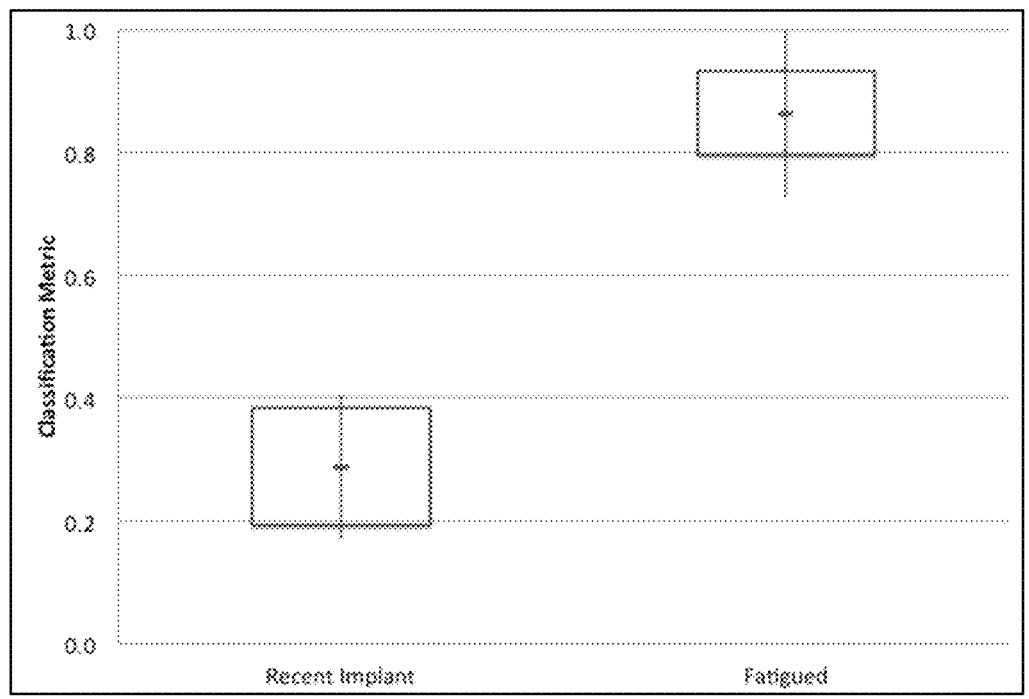

The results for Metric 4 (ratio of the sum of events in Clusters 1 and 4 with the sum of events in Clusters 2 and 3, offset of unity) are shown in Table 5. FIG. 19 illustrates a "box and whisker" plot of the data in Table 5. Metric 4 also shows clear discrimination between Fatigued state and Recent and Functional state of the implants.

TABLE 5

Metric 4, Results
Ratiometric Metric Values

| Recent and Functional State | | Fatigued State | |
|---|---|---|---|
| Subject ID | Value | Subject ID | Value |
| 1020 Left | 2.7 | 1029 Right | 15.7 |
| 1022 Right | 4.0 | 1030 Right | 11.4 |
| 1025 Left | 2.7 | | |
| 1025 Right | 5.0 | | |
| 1029 Left | 6.4 | | |
| 1029 Right | 6.3 | | |

As seen in Tables 2-5 above, Metrics 1-4 are effective for discrimination between Fatigued implants and those classified as Recent or Functional.

Figure 20:
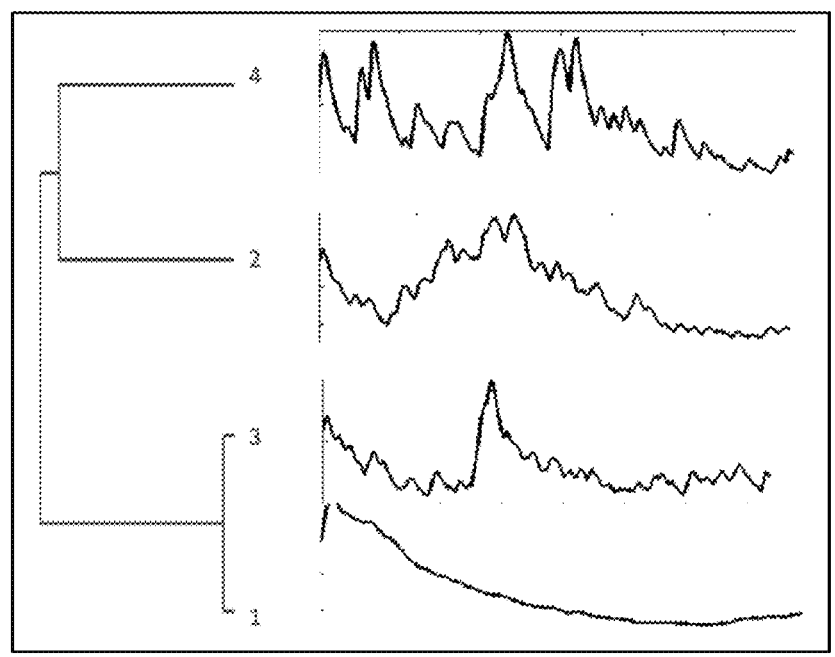
FIG. 20 illustrates an example of a dendrogram and corresponding event silhouettes.
Figure 21:
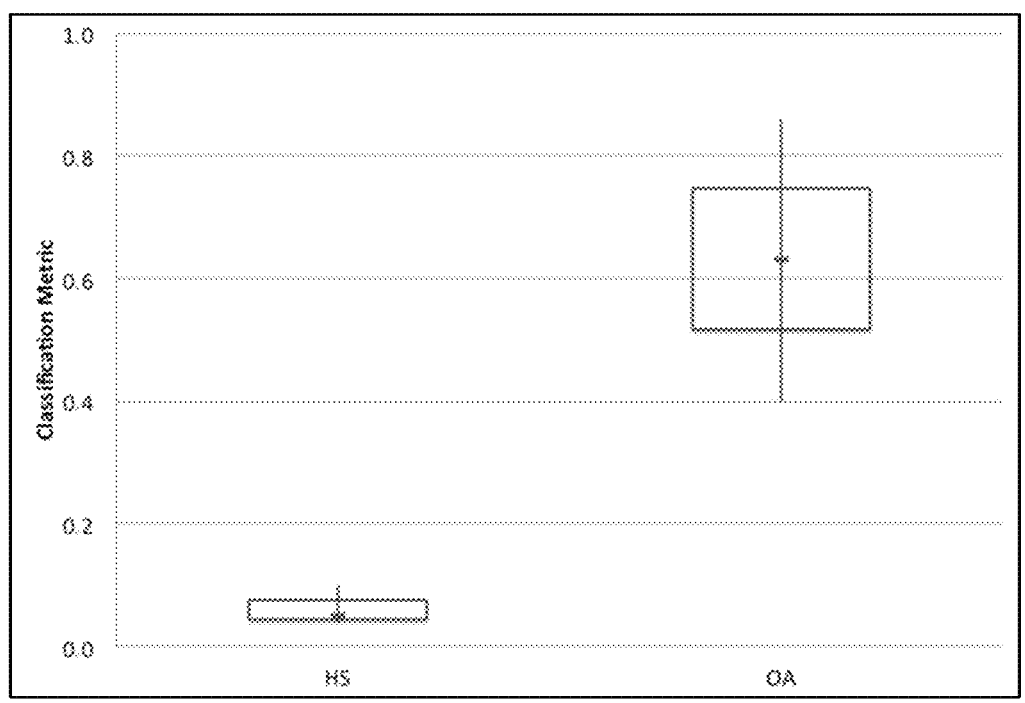
FIG. 21 illustrates an example of a "box and whisker" plot of cluster data.

The Orthosonos technique was also used in trials including both healthy subjects and those diagnosed with osteoarthritis. Event distribution for the trials is shown in Table 6. Data from these subjects was used to create a dendrogram as shown in FIG. 20, with corresponding Event Silhouettes. Classification of joint state was based on a metric that included the count of assignments in Cluster 1 of the dendrogram. The populations in Cluster 1 and Cluster 2 scale directly with joint state for this population, as shown in the "box and whisker" plot in FIG. 21 which indicates the maximum and minimum values as well as the average value. FIG. 21 illustrates a large separation between average values, and the data further shows that the first and third quartiles are well separated.

TABLE 6

| | | Event Distribution Within Clusters | | | |
|---|---|---|---|---|---|
| | Subject State | Cluster1 | Cluster2 | Cluster3 | Cluster4 |
| 1003 | Healthy | 8 | 1 | 0 | 0 |
| 1006 | Healthy | 4 | 0 | 0 | 0 |
| 1008 | Healthy | 3 | 0 | 0 | 0 |
| 1015 | Osteoarthritic | 69 | 5 | 3 | 1 |
| 1027 | Osteoarthritic | 32 | 1 | 1 | 0 |

Figure 22A:
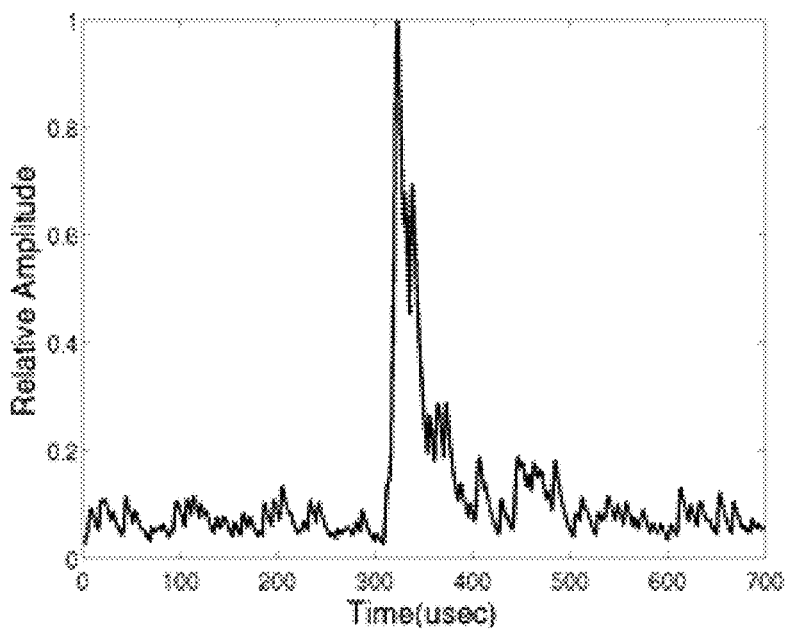
FIGS. 22A-C illustrate an example of a sensor signal (FIG. 22A), with corresponding power spectral density (PSD) (FIG. 22B) and cumulative distribution function (CDF) (FIG. 22C).
Figure 22B:
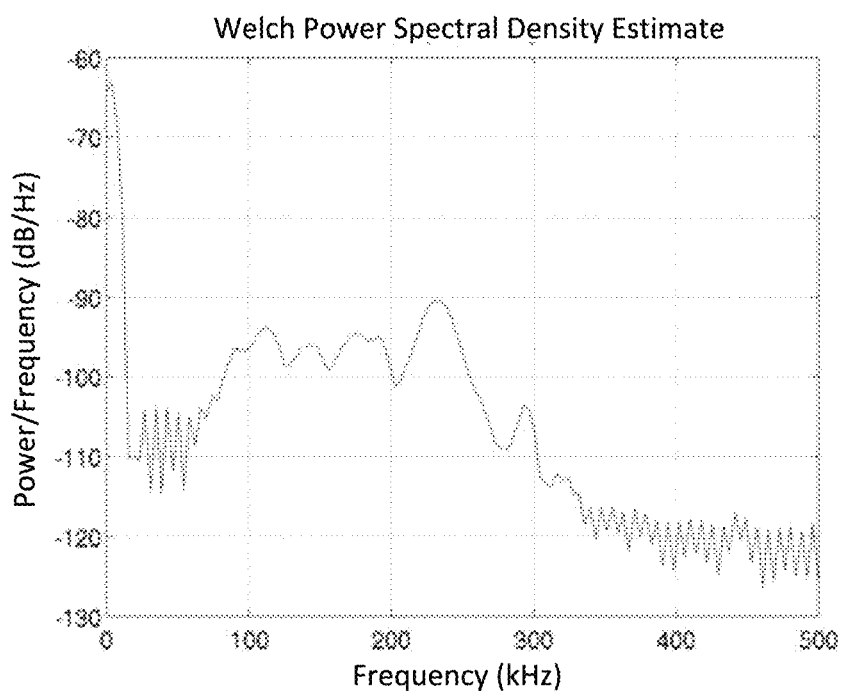
Figure 22C:
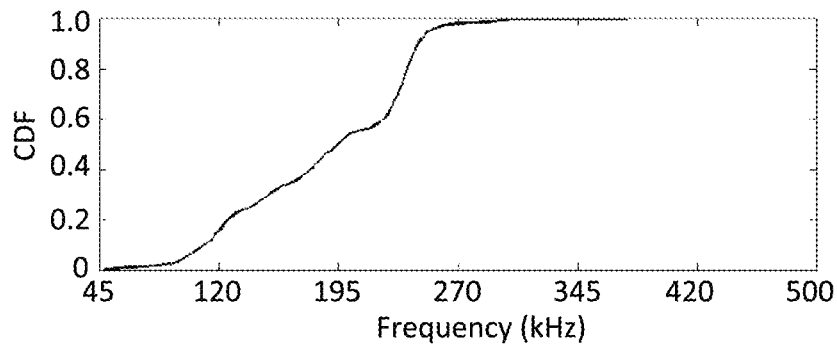
Figure 23A:
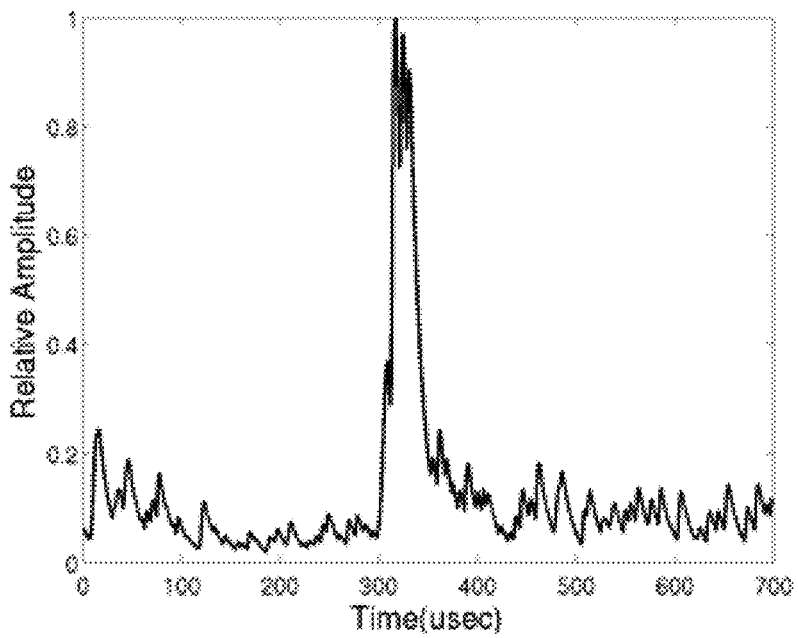
FIGS. 23A-C, 24A-C, 25A-C, 26A-C, and 27A-C illustrate other examples of sensor signals with corresponding PSD and CDF.
Figure 23B:
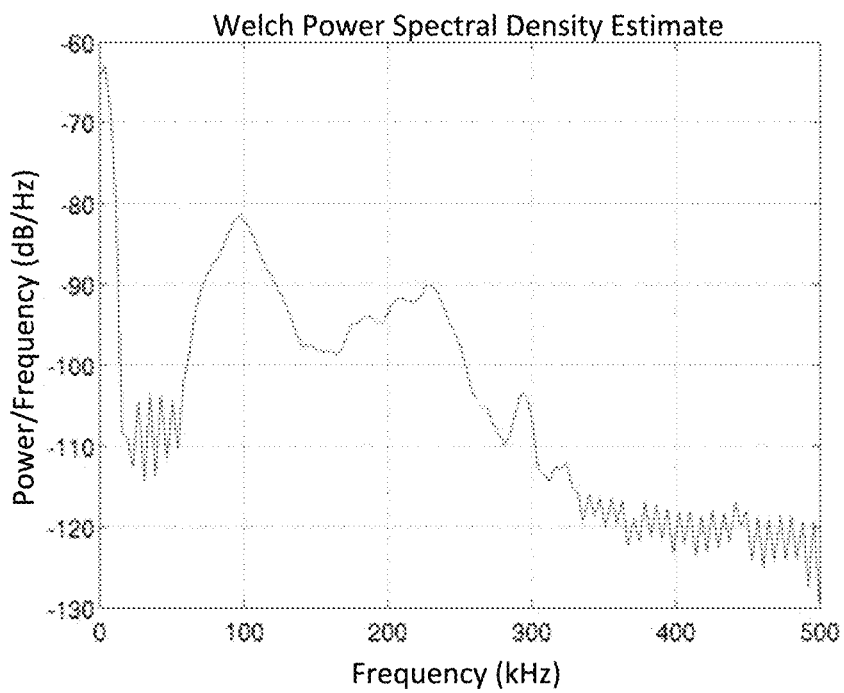
Figure 23C:
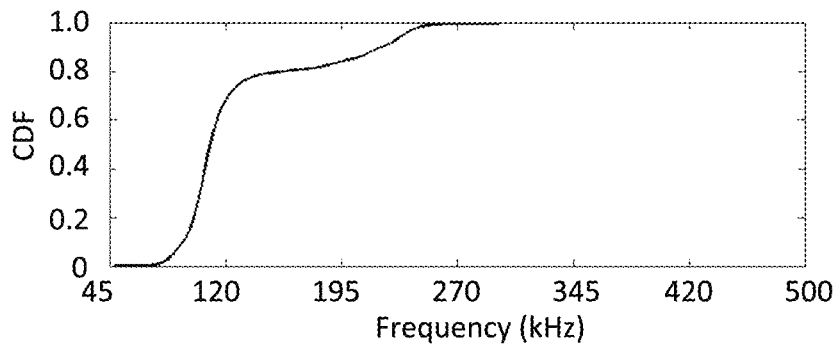
Figure 24A:
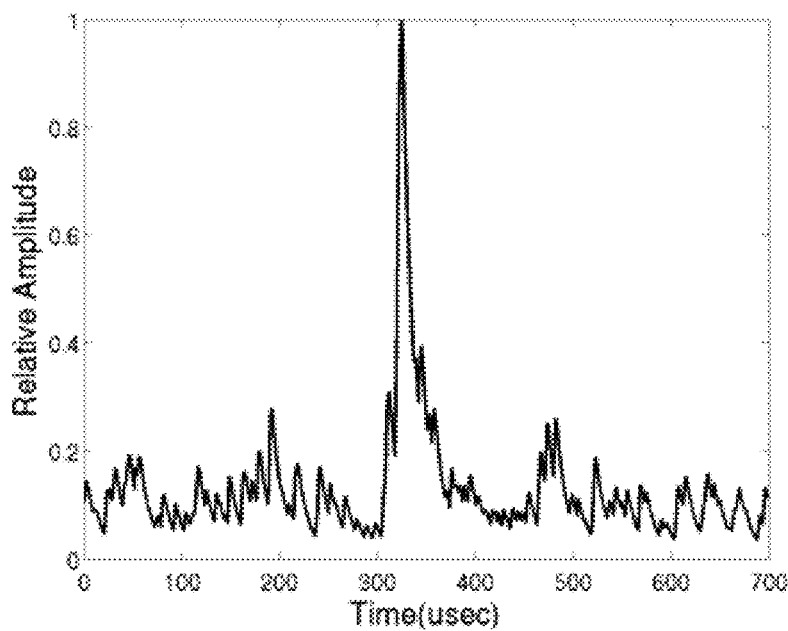
Figure 24B:
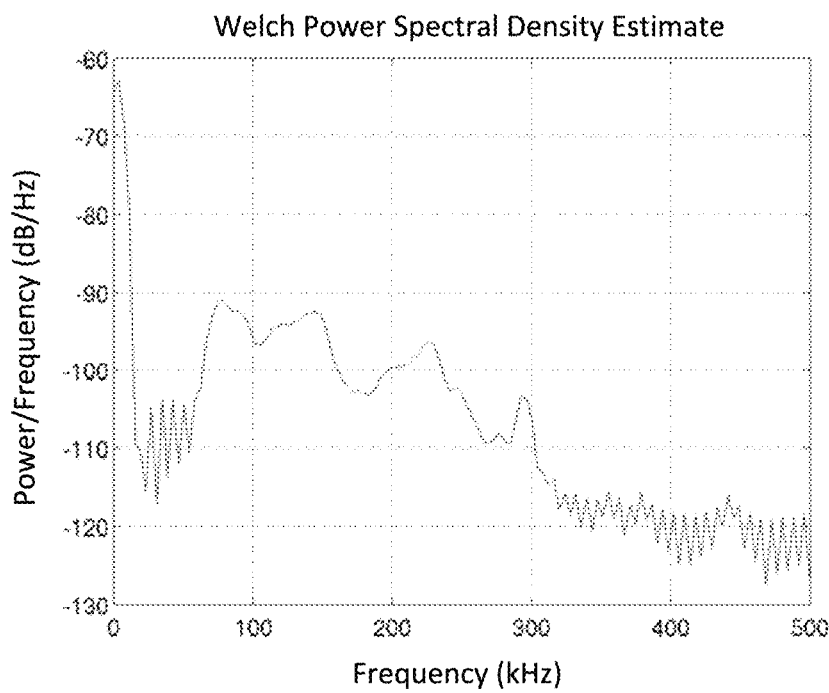
Figure 24C:
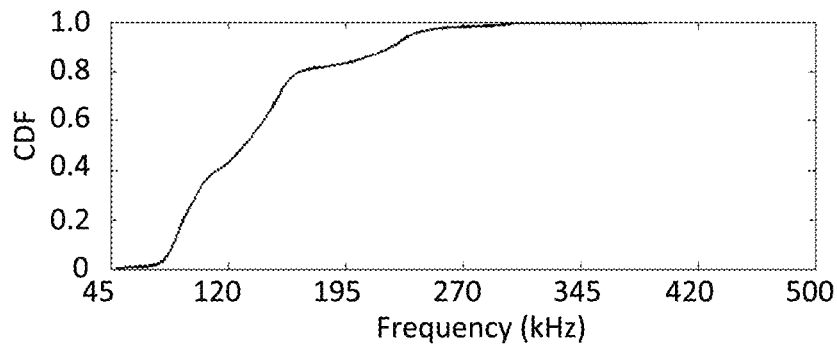
Figure 25A:
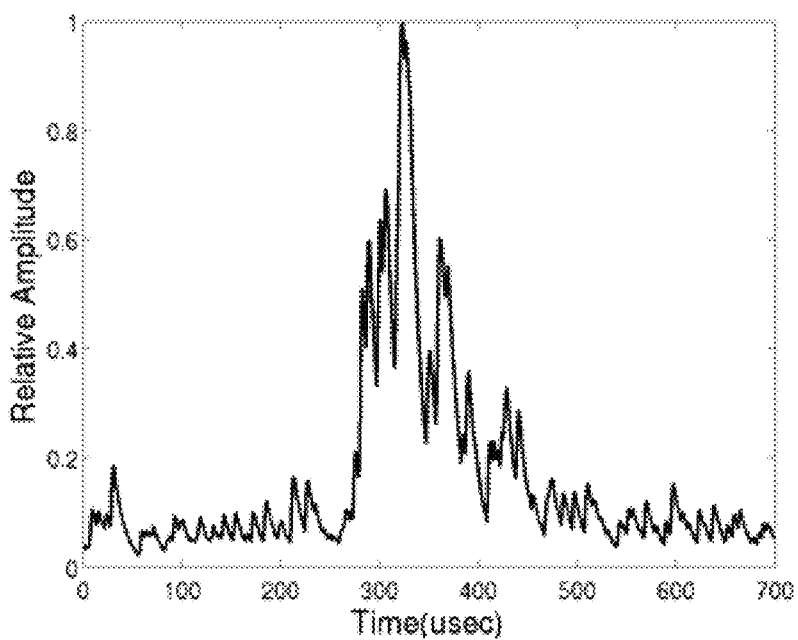
Figure 25B:
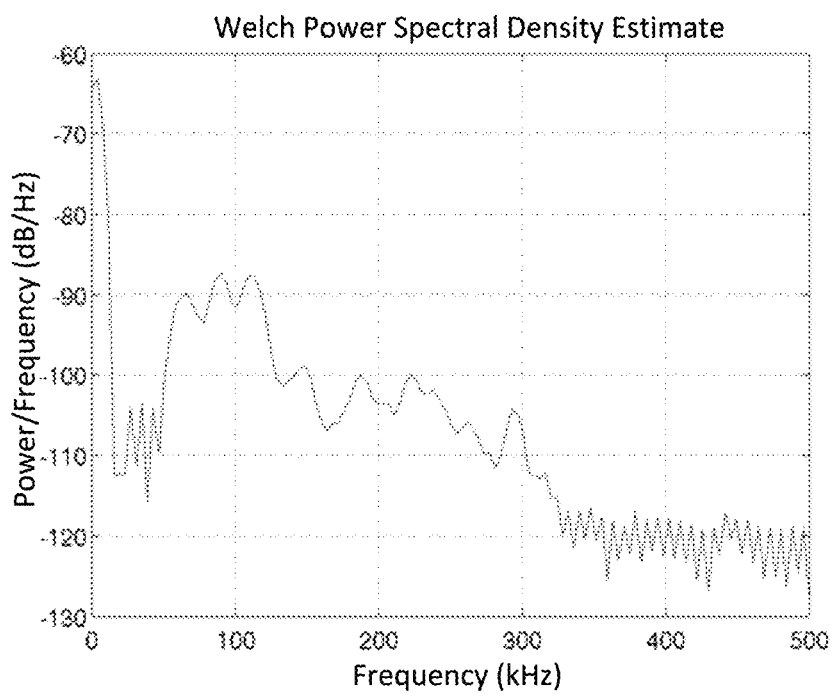
Figure 25C:
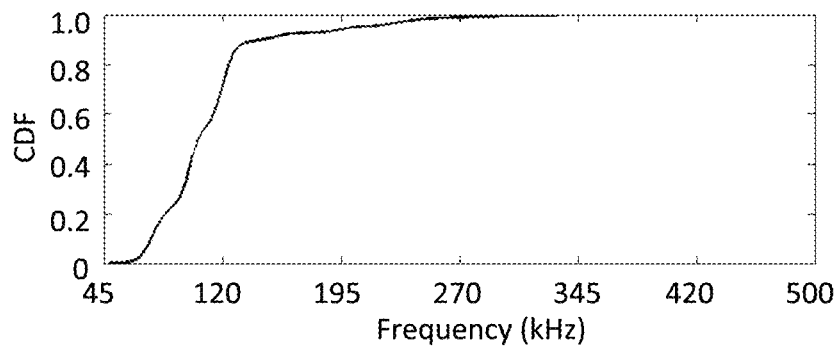
Figure 26A:
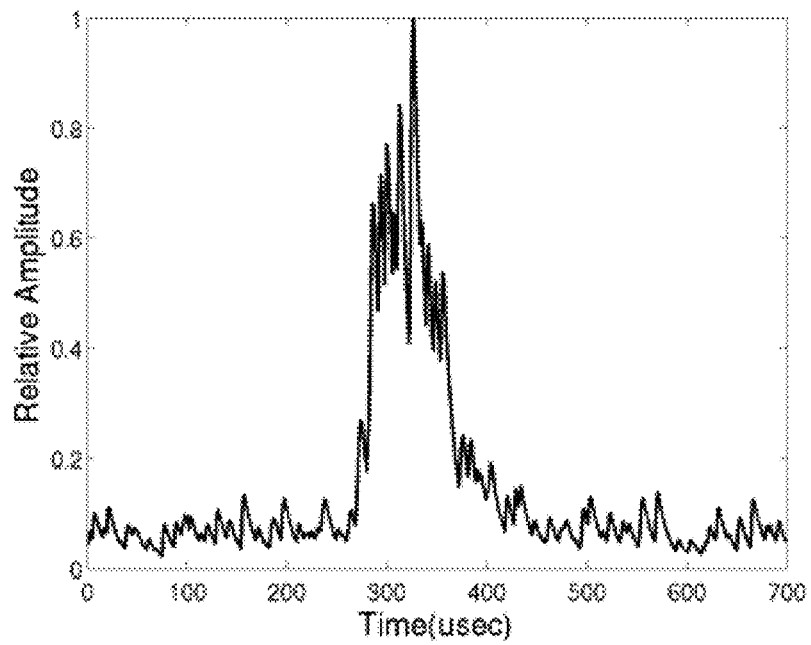
Figure 26B:
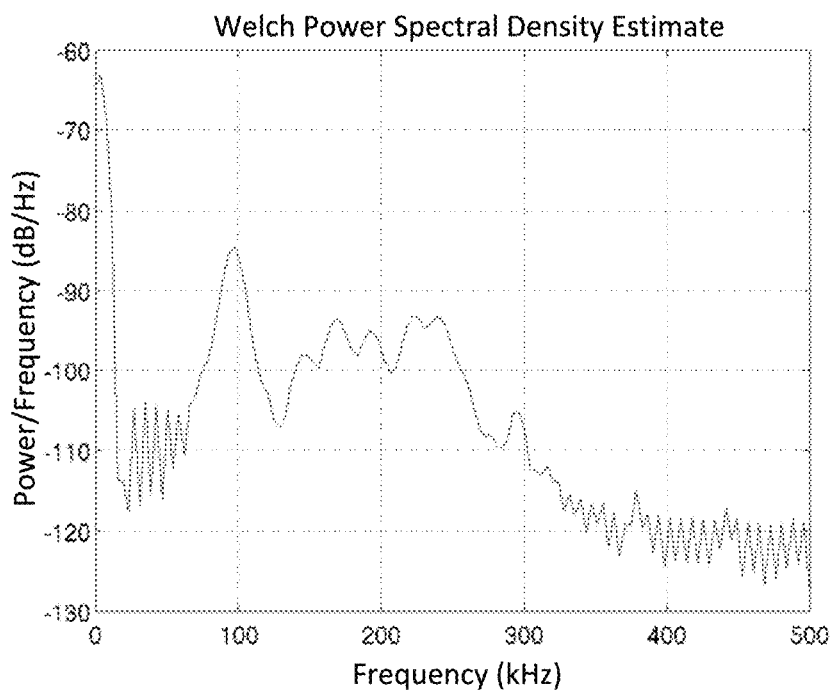
Figure 26C:
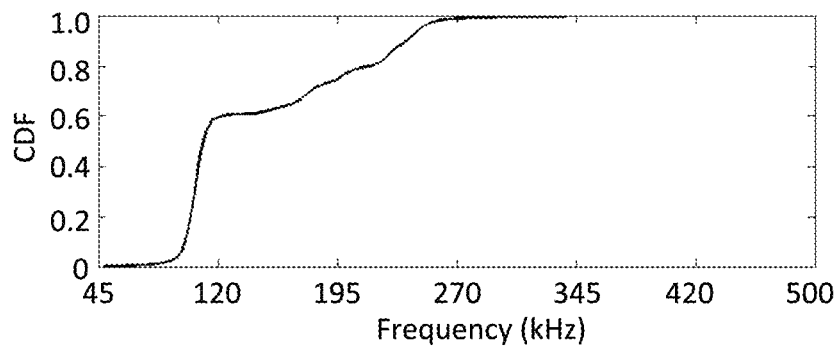
Figure 27A:
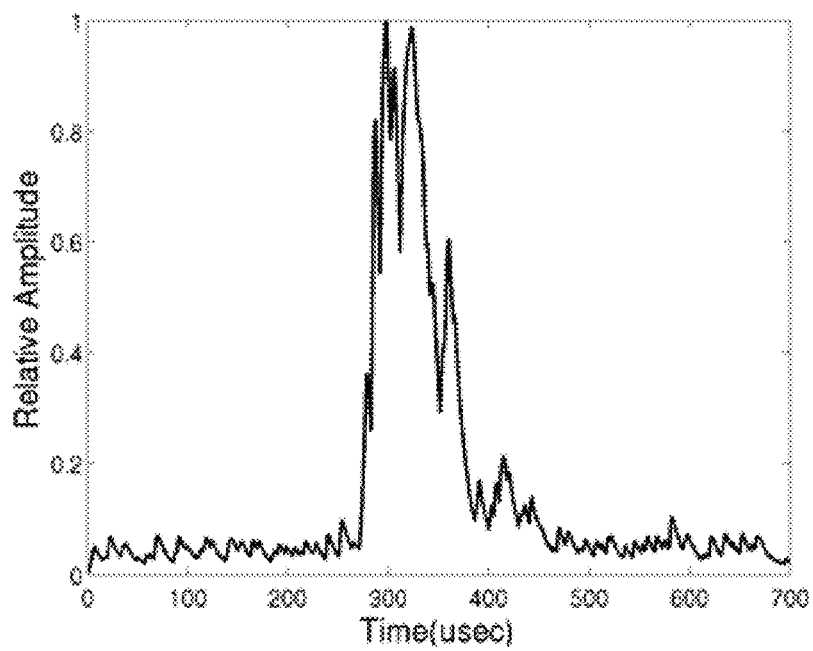
Figure 27B:
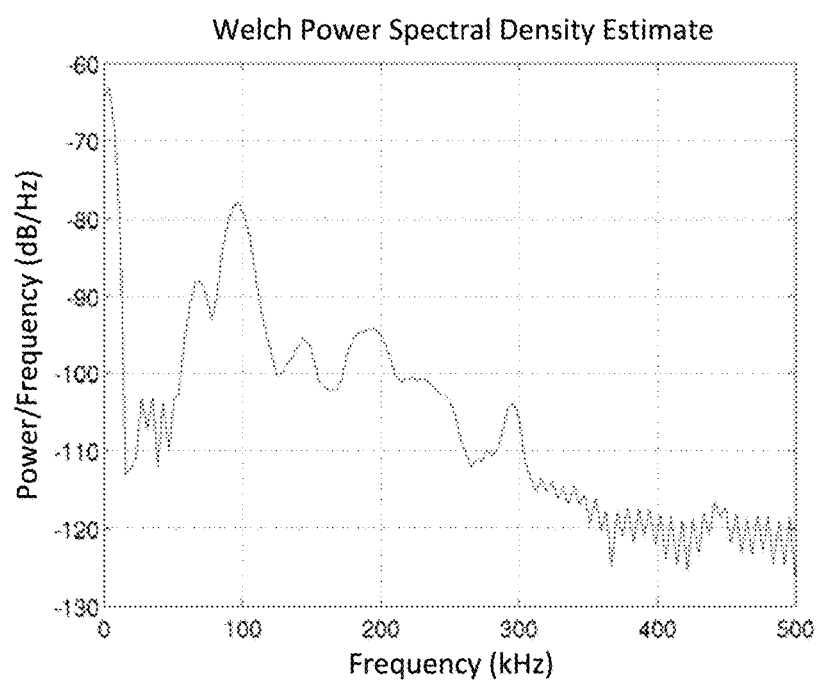
Figure 27C:
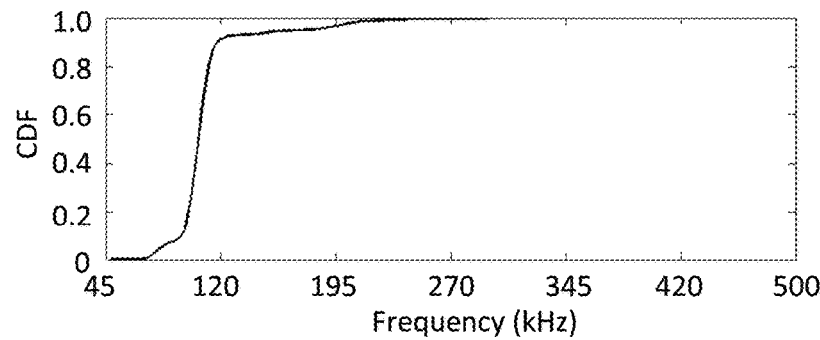

FIGS. 22A-C shows a time domain Event Envelope (FIG. 22A), with the corresponding power spectral density (PSD) characteristics (FIG. 22B) and the cumulative distribution function (CDF—the probability that a PSD amplitude is less than a value) (FIG. 22C), for a test of a sit-to-stand maneuver. FIGS. 23-24 similarly show time domain envelope, PSD, and CDF for other tests of the sit-to-stand maneuver. FIGS. 25-27 show time domain envelope, PSD, and CDF for tests of knee flex. As can be seen in FIGS. 22-27, CDF yields a discrimination system that is amplitude independent and that can be used in combination with time domain envelopes for classification.

It is important to have the capability to detect and reject noise that appears as AE events, referred to herein as noise events. Noise events are therefore identified. For example, noise events are identified for knee-flex and hip-flex maneuvers by supporting a subject's leg and manually elevating and lowering the leg. Because joint forces are negligible during this maneuver, it is expected that events will be due to sources of AE external to the joint (i.e., noise). FIGS. 28 and 29 illustrate a signal silhouette and a noise silhouette (FIGS. 28A, 29A, respectively), with corresponding CDF (FIGS. 28B, 29B, respectively), developed to aid in discrimination between signal events and noise events.

Figure 30:
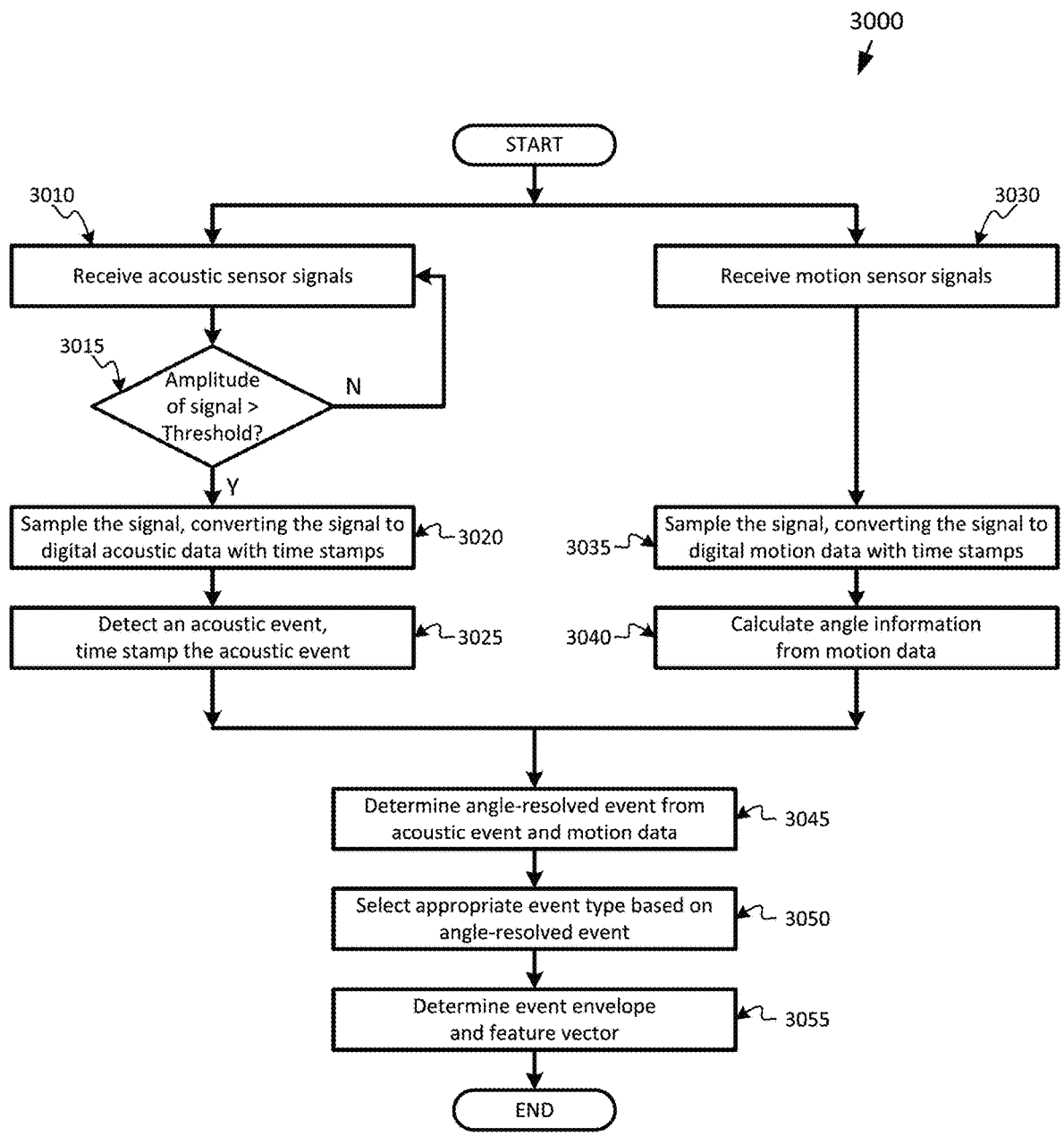
FIG. 30 illustrates an example of determining event envelopes and descriptors.
Figure 31A:
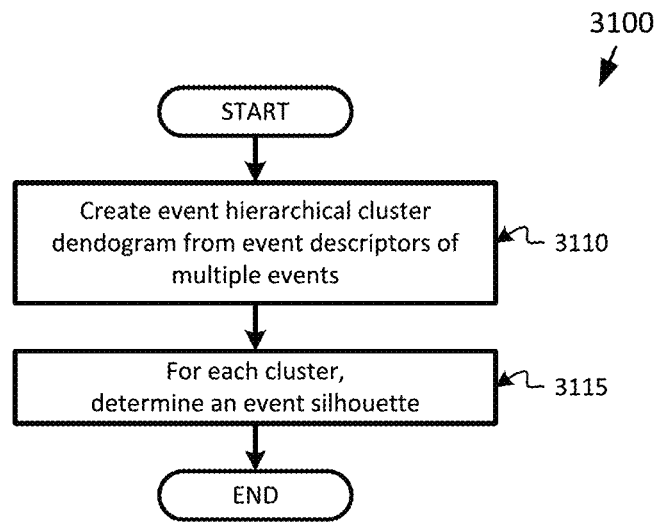
FIG. 31A illustrates an example of determining an event silhouette.
Figure 31B:
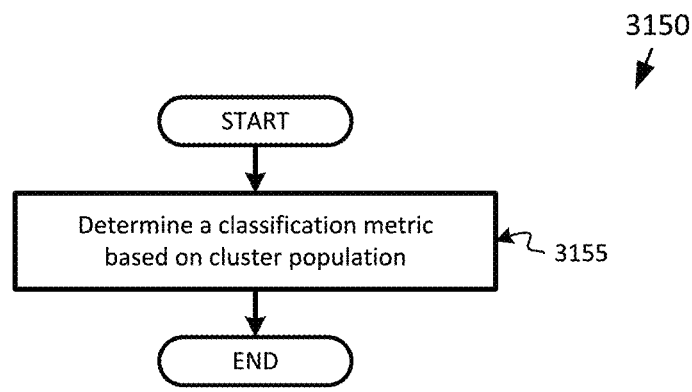
FIG. 31B illustrates an example of determining a classification metric.
Figure 32:
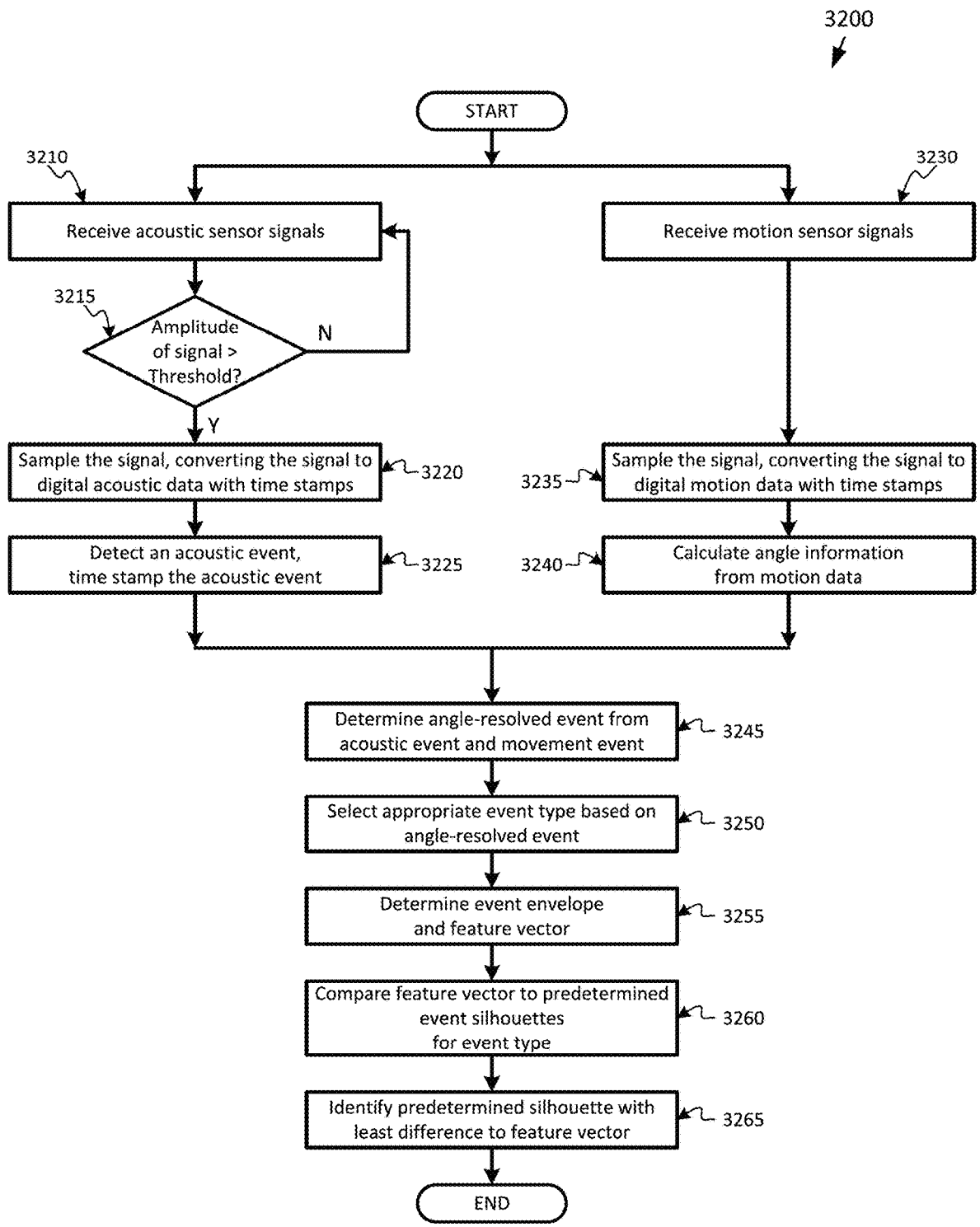
FIG. 32 illustrates an example of identifying an event envelope with a silhouette.

FIGS. 30-32 are provided by way of illustration, to demonstrate how the techniques described in this disclosure may be implemented.

FIG. 30 illustrates an example of a technique 3000 for gathering and preparing data from sensors in a SEARI system, such as an Orthosonos or other system.

At block 3010, one or more acoustic sensor signals are received, such as via an acquisition interface 140 (FIG. 1). An acoustic signal is compared to a threshold at block 3015, and if the acoustic signal is greater than the threshold, it is sampled, converted to digital acoustic data (e.g., via an ADC), and time stamped at block 3020. Otherwise, the acoustic signal is not sampled. From the digital acoustic data, an acoustic event is detected and time stamped at block 3025 (see, for one example of detecting acoustic events, the description of FIG. 11).

At block 3030, one or more motion sensor signals are received. The motion sensor signals are sampled, converted to digital motion data (e.g., via an ADC), and time stamped at block 3035. From the digital motion data, angle information is calculated.

Blocks 3010 and 3030 are generally concurrent, in that signals from acoustic and motion sensors may be received continuously. The signals may be sampled (blocks 3020, 3035) periodically, semi-periodically, randomly, or at the occurrence of an event, such as the expiration of a timer or, in the case of the acoustic signals, the occurrence of an acoustic signal greater than the threshold. Blocks 3020 and 3035 may be, but are not necessarily, performed substantially concurrently, where concurrent includes performance using parallel or interleaved A/D conversion and/or processing. For example, while waiting for an acoustic signal that exceeds the threshold (block 3015), no sampling is being performed at block 3020 for the acoustic signal(s); however, sampling may be performed (e.g., at a 100 Hz sample rate) at block 3035 for the motion sensor signal(s)—therefore there is not concurrent performance in this example. In a contrasting example, when an acoustic signal exceeds the threshold, the acoustic signal is sampled at block 3020; concurrently, a periodic sampling of the motion sensor signal(s) may be occurring at block 3035.

At block 3045, the time-stamped acoustic event detected in block 3025 and the angle information from block 3040 are used to determine an angle-resolved event, which in turn is used to select an event type at block 3050 that is appropriate for the angle-resolved event. At block 3055, an Event Envelope and feature vector are determined for the angle-resolved event.

At the end of technique 3000, an acoustic event is described by event type, Event Envelope, and feature vector. Multiple acoustic events may be used to create clusters. FIG. 31A illustrates at block 3110 that feature vectors from multiple acoustic events are used to create a hierarchical dendrogram of clusters, and at block 3115, an Event Silhouette is determined for each cluster in the dendrogram. A dendrogram and associated Event Silhouettes may be determined from multiple acoustic events of one subject or multiple subjects.

FIG. 31B illustrates by way of technique 3150 that a classification metric may be determined based on cluster populations, where the cluster populations are generally determined from acoustic events of multiple subjects.

After clustering and silhouetting is performed, acoustic events detected at a later time may be compared to the Event Silhouettes to classify the later acoustic events. For example, acoustic events may be monitored for a period of time and compared to a baseline created from multiple acoustic events of the subject to analyze the status or trend in healing of a joint.

FIG. 32 illustrates a technique 3200 for classifying a later acoustic event. Blocks 3210-3240 are performed similarly to blocks 3010-3040, and are not described in detail. It is not necessary that blocks 3210-3240 are performed with the same or similar system as used to perform blocks 3010-3040, nor is it necessary that the same parameters are used. For example, the threshold used (blocks 3015, 3215) may depend on environment, such that the threshold changes with noise (e.g., is equal to average of noise amplitude, or average of peak noise amplitude, or a multiple of an average amplitude). For another example, sampling rates for sampling the motion sensor signals may be different, and the different sampling rates compensated for by processing (e.g., decimation, padding, etc).

At blocks 3245-3255, similarly to blocks 3045-3055, the time-stamped acoustic event detected in block 3225 and the angle information from block 3240 are used to determine an angle-resolved event, which in turn is used to select an event type appropriate for the angle-resolved event.

At block 3260, the determined feature vector (block 3255) for the acoustic event is compared to Event Silhouettes previously determined for the event type, and, at block 3265, the previously-determined Event Silhouette with the least difference to the determined feature vector for the later acoustic event is identified. Therefore, technique 3200 allows for the classification of acoustic events.

Conclusion

A SEARI system provides an accurate, flexible, and versatile system for monitoring the state of implants, natural and artificial joints, the spine, bones, cartilage, organs, and other tissue. The ability to monitor patients during normal activity outside the confines of a laboratory enables a SEARI system to be used in a number of novel ways, including in athletics. For example, a SEARI system may be used in performance improvement, direct strengthening exercises, and customization of rehabilitation exercises for injury recovery.

A SEARI system in combination with, or including, an EMAE or ultrasonic source may be used, for example, to monitor growth plate injury and healing in young subjects, replacing the costly and relatively ineffective tests that are currently used. In another example, a SEARI system may be used in detecting slipped capital femoral epiphysis, thereby avoiding misdiagnoses that may lead to occlusion of blood supply and avascular necrosis.

Coupled with highly localized ultrasound sources (e.g., vibro-acoustography), a SEARI system may be used to obtain acoustic images of tissues over a period of time and at a much lower cost relative to other imaging techniques.

A SEARI system allows clinicians to remotely monitor patients, reducing the need for clinic and hospital visits.

It will be apparent from the figures and description in this disclosure that a SEARI system, although described in the context of medical monitoring, may be used also for monitoring in other fields of endeavor, such as for monitoring non-human animals, monitoring mechanical devices other than prosthetic and fixation devices, monitoring fluid flow, and monitoring other structures and materials that exhibit AE.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure

What is claimed is:

1. An apparatus, comprising:
   an acoustic sensor configured to receive an acoustic signal;
   an input-output interface coupled to the acoustic sensor and configured to detect an emission and save the emission as a sample event buffer set; and
   a processor coupled to the input-output interface and configured to receive the sample event buffer set, wherein the processor is further configured to:
   calculate in the time domain an event envelope from the sample event buffer set by taking a square root of a sum of squares of the sample event buffer set and respective Hilbert Transforms of the sample event buffer set in the time domain,
   determine a plurality of vector elements that form a feature vector in the time domain that measures an amplitude of the event envelope in the time domain,
   calculate a Euclidean distance between the feature vector in the time domain and each of a set of predetermined event silhouettes, and
   identify one of the predetermined event silhouettes for which the Euclidean distance is a minimum.

2. The apparatus of claim 1, wherein the processor is further configured to identify a sample event buffer set as being related to the acoustic event when the sample event buffer set is above a threshold value related to noise.

3. The apparatus of claim 1, further comprising a computer-readable storage medium.

4. The apparatus of claim 3, wherein the sample event buffer set is stored in the computer readable storage medium with time stamps.

5. The apparatus of claim 1, wherein the processor is further configured to normalize the feature vector by dividing the vector elements by a maximum amplitude of the vector elements.

6. The apparatus of claim 1, wherein the apparatus is part of a prosthetic device.

7. The apparatus of claim 6, wherein the prosthetic device is implantable in a human body.

8. The apparatus of claim 1, wherein the apparatus is part of a fixation device for application to a human body.

9. The apparatus of claim 1, wherein the apparatus is part of a fixation device for implantation partially or fully within a human body.

10. The apparatus of claim 1, wherein the apparatus monitors a tissue selected from the group consisting of: a natural joint, an artificial joint, a spine, a bone, a cartilage, and an organ.

11. The apparatus of claim 1, wherein the acoustic sensor is configured for detecting a range of at least 100-500 kHz.

12. The apparatus of claim 1, wherein the acoustic signal is at least 100 kHz.

13. The apparatus of claim 1, further comprising a motion sensor configured to receive a motion signal.

14. The apparatus of claim 13, further comprising a second processor configured to interface with the motion sensor such that receipt of the motion signal can be synchronized with the receipt of the acoustic signal.

15. The apparatus of claim 13, further comprising a high-rate analog-to-digital conversion (ADC) unit configured to convert the acoustic signal and motion signal into digitized acoustic data and digitized motion data, respectively.

16. The apparatus of claim 15, wherein the digitized acoustic data comprise a plurality of time stamped acoustic signals, and wherein the digitized motion data comprise a plurality of time-stamped motion signals.

17. The apparatus of claim 11, wherein the processor is further configured to determine a health status of a natural or artificial portion of a human body.

18. The apparatus of claim 1, further comprising a sensor selected from the group consisting of: a piezoelectric (PZT) sensor and an electromyography sensor.

* * * * *